(12) United States Patent
Miller

(10) Patent No.: US 8,911,988 B2
(45) Date of Patent: Dec. 16, 2014

(54) MENSTRUAL FLUID ANALYSIS

(75) Inventor: Seth Adrian Miller, Englewood, CO (US)

(73) Assignee: Empire Technology Development LLC, Wilmington, DE (US)

(*) Notice: Subject to any disclaimer, the term of this patent is extended or adjusted under 35 U.S.C. 154(b) by 0 days.

(21) Appl. No.: 13/202,559

(22) PCT Filed: Mar. 1, 2011

(86) PCT No.: PCT/US2011/026716
§ 371 (c)(1),
(2), (4) Date: Aug. 19, 2011

(87) PCT Pub. No.: WO2012/118494
PCT Pub. Date: Sep. 7, 2012

(65) Prior Publication Data
US 2013/0331666 A1  Dec. 12, 2013

(51) Int. Cl.
C12M 1/34 (2006.01)
A61B 5/145 (2006.01)
A61B 5/15 (2006.01)
A61B 5/00 (2006.01)
G01N 33/49 (2006.01)
A61F 13/84 (2006.01)
A61F 13/42 (2006.01)
G01N 33/52 (2006.01)
A61B 10/00 (2006.01)

(52) U.S. Cl.
CPC .......... *A61B 5/14546* (2013.01); *A61B 5/1405* (2013.01); *A61B 5/150045* (2013.01); *A61B 5/150755* (2013.01); *A61B 5/150969* (2013.01); *A61B 5/14507* (2013.01); *A61B 5/6808* (2013.01); *G01N 33/49* (2013.01); *A61F 13/84* (2013.01); *A61F 13/42* (2013.01); *G01N 33/528* (2013.01); *A61B 2010/0074* (2013.01); *A61F 2013/8473* (2013.01)
USPC ......................................... 435/288.7; 600/587

(58) Field of Classification Search
USPC .................................. 435/12, 288.7; 600/587
See application file for complete search history.

(56) References Cited

U.S. PATENT DOCUMENTS 3,850,160 A   11/1974   Denson
3,929,135 A   12/1975   Thompson
(Continued)

FOREIGN PATENT DOCUMENTS

DE   102004032253   1/2006
WO   2004092342   10/2004

OTHER PUBLICATIONS

Law, W. T. et al., "Whole-blood Test for Total Cholesterol by a Self-metering, Self-timing Disposable Device with Built-in Quality Control," Clinical Chemistry, 1997, pp. 384-389, vol. 43.

(Continued)

*Primary Examiner* — Max Hindenburg
*Assistant Examiner* — Renee Danega
(74) *Attorney, Agent, or Firm* — Foley & Lardner LLP

(57) ABSTRACT

A disposable menstrual fluid fractionation apparatus for use in situ during menstruation is disclosed. The apparatus may include a filter configured to remove a particulate component of menstrual fluid from a liquid component of the menstrual fluid. A receptacle may be coupled to the filter. The filter, receptacle, and an analyte sensor may be integrated into a disposable feminine hygiene product. The integrated analyte sensor may be configured to detect a target analyte in the liquid component and indicate the presence/concentration of the target analyte.

27 Claims, 10 Drawing Sheets

(56) References Cited

U.S. PATENT DOCUMENTS

| | | | |
|---|---|---|---|
| 4,342,314 | A | 8/1982 | Radel et al. |
| 4,609,518 | A | 9/1986 | Curro et al. |
| 4,629,643 | A | 12/1986 | Curro et al. |
| 4,795,455 | A | 1/1989 | Luceri et al. |
| 5,468,236 | A | 11/1995 | Everhart et al. |
| 5,985,675 | A | 11/1999 | Charm et al. |
| 6,174,293 | B1 | 1/2001 | Buck et al. |
| 6,186,991 | B1 | 2/2001 | Roe et al. |
| 6,426,227 | B1 | 7/2002 | Kritzman et al. |
| 6,627,790 | B2 | 9/2003 | Bouchard et al. |
| 6,713,660 | B1 | 3/2004 | Roe et al. |
| 6,812,169 | B2 * | 11/2004 | Potts et al. .................. 442/118 |
| 6,921,647 | B2 * | 7/2005 | Kritzman et al. ............... 435/12 |
| 7,605,004 | B2 | 10/2009 | Zhou |
| 2004/0172000 | A1 | 9/2004 | Roe et al. |
| 2006/0246600 | A1 | 11/2006 | Yang et al. |
| 2009/0142229 | A1 | 6/2009 | MacDonald et al. |
| 2010/0015658 | A1 | 1/2010 | Yang et al. |
| 2010/0089815 | A1 | 4/2010 | Zhang et al. |

OTHER PUBLICATIONS

Allen, M.P. et al., "A Noninstrumented Quantitative Test System and its Application for Determining Cholesterol Concentration in Whole Blood," Clinical Chemistry, 1990, pp. 1591-1597, vol. 36, No. 9.

Craig Medical Distribution, Inc., "Venture Home Cholesterol Test," Product description, Oct. 2001, 3 pages.

International Search Report and Written Opinion, issued in International Patent Application No. PCT/US2011/026716, mailed Jun. 14, 2011, 17 pages.

Carter et al., "Lateral Flow Microarrays: a Novel Platform for a Rapid Nucleic Acid Detection Based on Miniaturized Lateral Flow Chromatography," Nucleic Acids Research, May 3, 2007, pp. 1-11, vol. 35, No. 10.

* cited by examiner

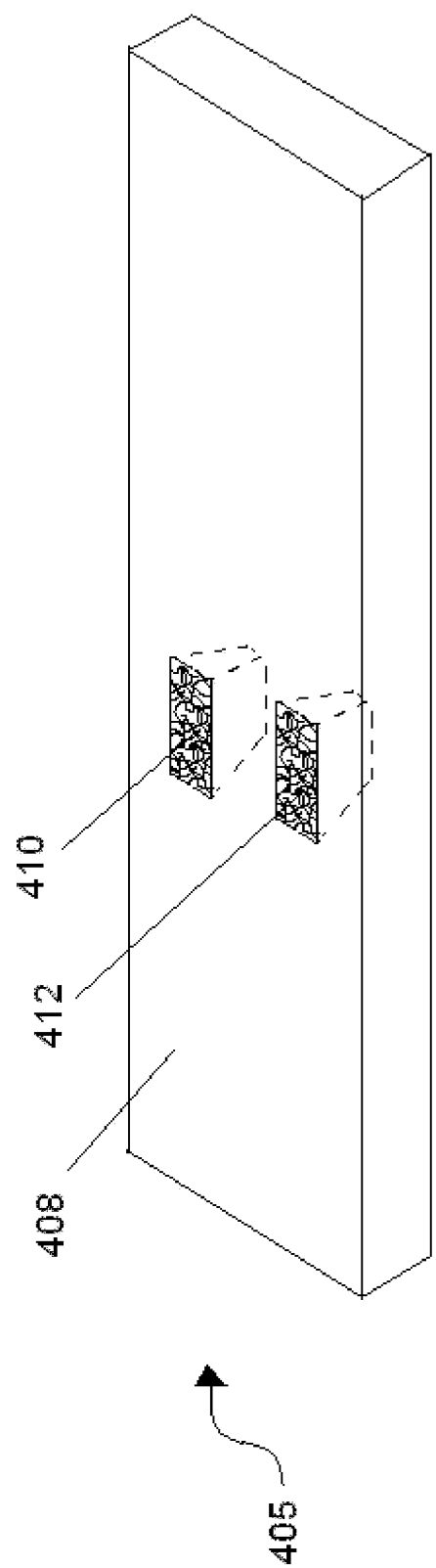

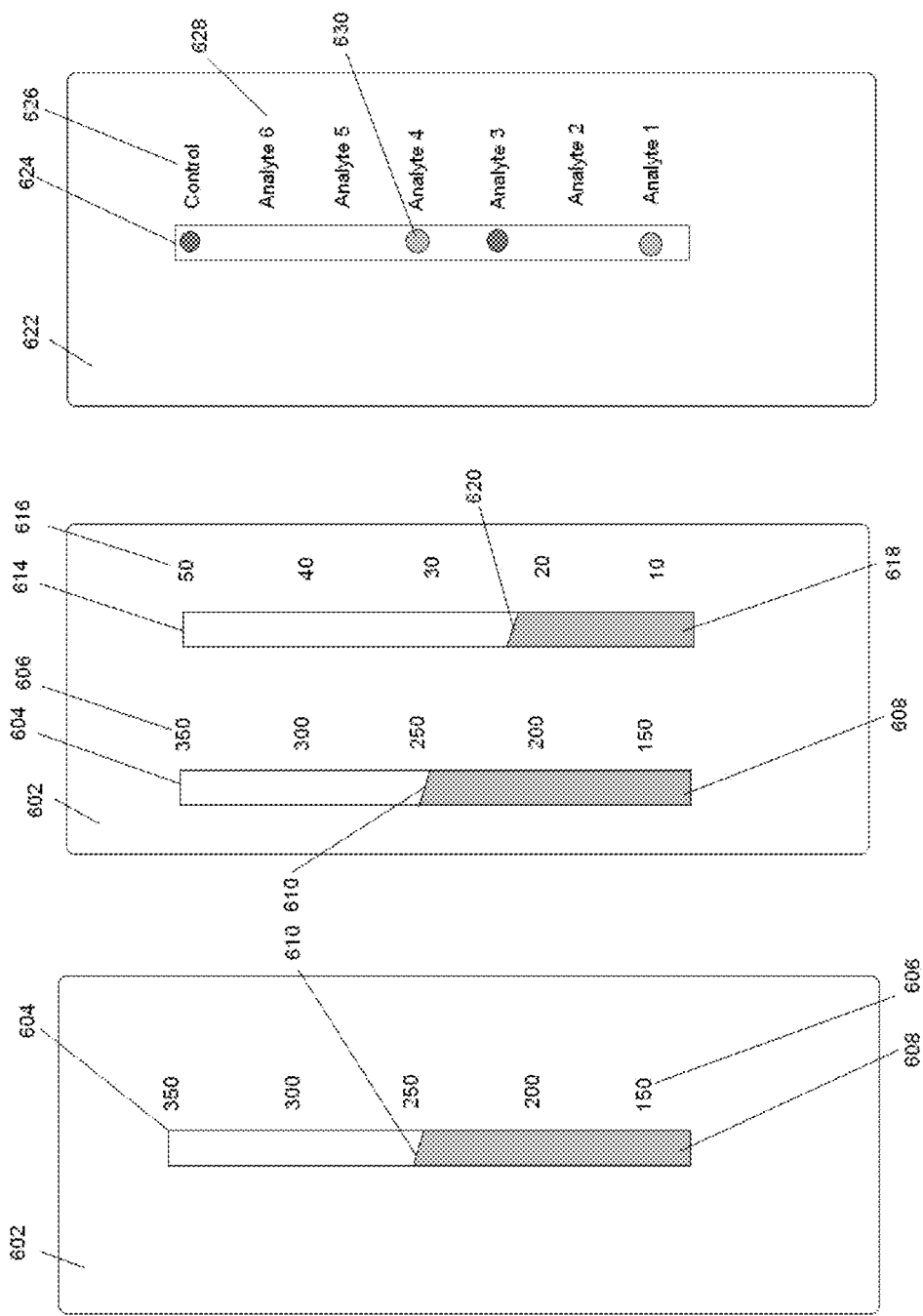

MENSTRUAL FLUID ANALYSIS

RELATED APPLICATIONS

This application is a 35 USC 371 national phase entry of PCT/US2011/026716, filed Mar. 1, 2011, which is incorporated herein by reference in its entirety.

BACKGROUND

Unless otherwise indicated herein, the materials described in this section are not prior art to the claims in this application and are not admitted to be prior art by inclusion in this section.

Biological fluids are frequently assayed to monitor or diagnose medical conditions. Collection of blood for diagnostic assays usually requires piercing of the patient's skin. Fear of sampling methods may deter patients from obtaining necessary medical testing, delaying or even preventing the diagnosis of potentially serious health conditions. Patients are often required to have the blood sample collected at a medical facility. The expense and inconvenience of this may further decrease compliance with recommended monitoring regimens.

BRIEF DESCRIPTION OF THE DRAWINGS

The presently disclosed subject matter is particularly pointed out and distinctly claimed in the concluding portion of the Specification. The foregoing and other features of the present disclosure will become more fully apparent from the following Detailed Description and appended Claims, taken in conjunction with the accompanying Figures. Understanding that these Figures depict examples in accordance with at least some embodiments of the disclosure and are, therefore, not to be considered limiting of its scope, the disclosure will be described with additional specificity and detail through use of the accompanying Figures.

FIGS. 4a-4c illustrate perspective views of filters for filtration of menstrual fluid in situ.

FIGS. 6a-6c illustrate plan views of a menstrual fluid assay display.

DETAILED DESCRIPTION

Figure 1:
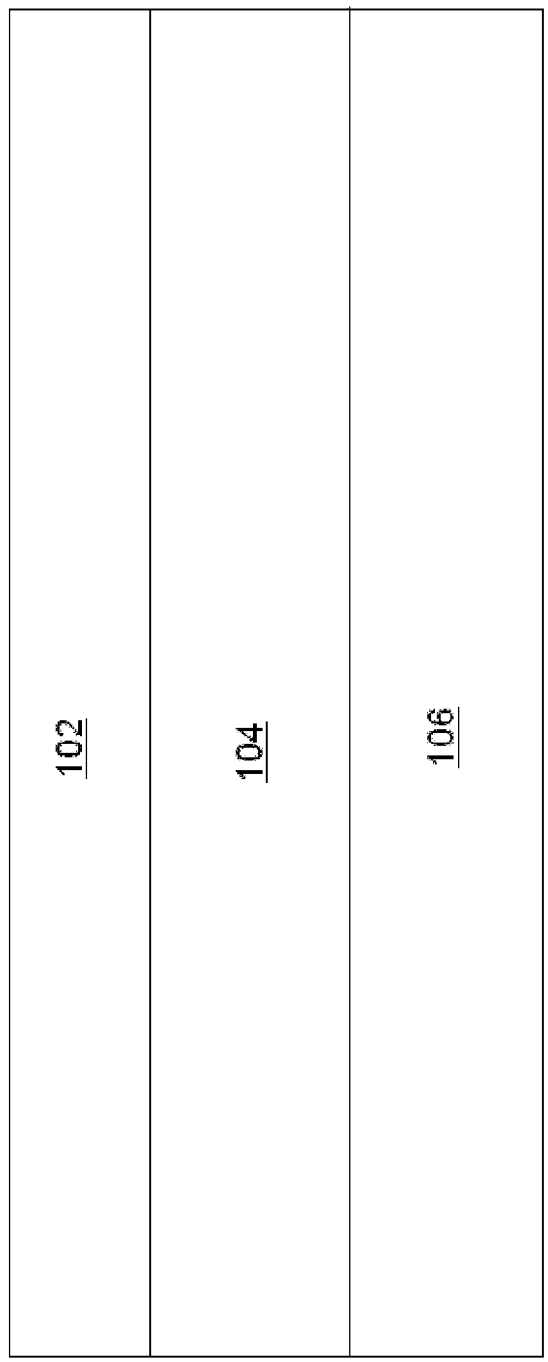
FIG. 1 illustrates a block diagram of an illustrative embodiment of a disposable article for filtration of menstrual fluid in situ.

The present Description sets forth various examples along with specific details to provide a thorough understanding of claimed subject matter. It will be understood by those skilled in the art, however, the claimed subject matter may be practiced without some or more of the specific details disclosed herein. Further, in some circumstances, well-known methods, procedures, systems, components and/or circuits have not been described in detail in order to avoid unnecessarily obscuring claimed subject matter. In the following Detailed Description, reference is made to the accompanying Figures, which form a part hereof. In the Figures, similar symbols typically identify similar components, unless context dictates otherwise. The illustrative embodiments described in the present Detailed Description, Figures, and Claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, may be arranged, substituted, combined, and designed in a wide variety of different configurations, all of which are explicitly contemplated and make part of this disclosure.

The present disclosure is drawn, inter alia, to methods, articles, and systems for the non-intrusive collection, fractionation, and analysis of menstrual fluid.

The present disclosure describes a disposable menstrual fluid fractionation apparatus. In some examples, a disposable menstrual fluid fractionation apparatus comprises a porous matrix, a receptacle, and a positioning element, and is configured to be coupled to a feminine hygiene product. The porous matrix includes an upstream surface with a first plurality of pores and a downstream surface with a second plurality of pores. The first and the second plurality of pores are permeable to a liquid component of a flow of menstrual fluid. The pores of the second plurality are impermeable to a mammalian erythrocyte, and have an average diameter less than the average diameter of the pores of the first plurality. The porous matrix may include one or more of an asymmetric microporous membrane and/or a stack of two or more porous membranes.

The receptacle is coupled to the downstream surface of the porous matrix and is configured to receive a portion of the liquid component after passage of the flow of menstrual fluid through the porous matrix. The receptacle may include a first detection reagent. The positioning element is coupled to the porous matrix, and is configured to retain the porous matrix between the receptacle and a flow of menstrual fluid. The positioning element may include one or more of an adhesive and/or an absorbent pad.

The apparatus may include a detection matrix coupled to the receptacle, and the detection matrix may include a second detection reagent. The apparatus may also include an absorbent layer coupled to the porous matrix. The absorbent layer is configured to receive a portion of the flow of menstrual fluid. In some examples, the apparatus includes a prefilter coupled to the upstream surface of the porous matrix. The prefilter has a third plurality of pores with an average diameter greater than the first plurality of pores and is impermeable to mammalian tissue. In some examples, the average diameter of the first plurality of pores is in the range of 5 µm to 50 µm, the average diameter of the second plurality of pores is in the range of 0.5 µm to 5 µm, and the average diameter of the third plurality of pores is in the range of 50 µm to 500 µm.

The present disclosure also describes a non-invasive menstrual fluid analyte monitoring system. Some example systems include an absorbent layer, a porous matrix, and an analyte sensor. The porous matrix is coupled to the absorbent layer and includes a first and a second plurality of pores, with the second plurality of pores having an average diameter of 5 µm or less. The analyte sensor is operatively coupled to the porous matrix and includes a detection matrix. Some systems may include a liquid-impermeable barrier operatively coupled to the porous matrix and the analyte sensor. The liquid-impermeable barrier is disposed between the porous matrix and the absorbent layer. Some systems may include a positioning element coupled to the absorbent layer. The positioning element is configured to retain the porous matrix in proximity to a flow of menstrual fluid. Example systems may include a display with a first surface and an opposite second surface. The first surface has a printed portion and the second surface is coupled to the detection matrix. The display may be removable from the analyte sensor. The printed surface portion may include a calibration scale.

Some systems may include a holder configured to retain the absorbent layer and porous matrix against a garment. The porous matrix may be an asymmetric membrane having an upstream surface with a first plurality of pores and a downstream surface with a second plurality of pores. The first plurality of pores may have an average diameter in the range of 5 µm to 50 µm and the second plurality of pores may have an average diameter in the range of 0.001 µm to 5 µm. The porous matrix may includes at least a first porous membrane having pores with an average diameter in the range of 5 µm to 50 µm and a second porous membrane having pores with an average diameter in the range of 0.001 µm to 5 µm. The porous matrix is at least partially surrounded by the absorbent layer.

In some systems, the analyte sensor further includes a receptacle disposed between the porous matrix and the detection matrix. The receptacle is liquid permeable and is provided with a first detection reagent specific to a target analyte. The detection matrix may be provided with a second detection reagent specific to the target analyte. The first detection reagent may include an indicator selected from the group consisting of a colored particle, a colloidal particle, an enzyme, and an enzyme substrate. Some example systems may include a prefilter coupled to the porous matrix and the absorbent layer, and may be integrated within a feminine hygiene product. At least one of the porous medium or the receptacle may be movably coupled to the analyte sensor.

The present disclosure also describes a method for manufacturing a menstrual fluid assay. Some example methods include providing a porous medium, coupling an absorbent layer to the porous medium, and coupling an analyte sensor to the porous medium. The porous medium has an upstream surface and a downstream surface, and the average diameter of the pores of the downstream surface is in the range of 0.001 µm to 5 µm. The porous medium is permeable to a liquid component of menstrual fluid. The analyte sensor includes a detection matrix and one or more detection reagents, and is configured to detect an analyte in the liquid component. Some methods include coupling a display to the detection matrix. The display is configured to provide a view of a visible indication of analyte detection by the analyte sensor. Some methods include coupling a solvent chamber to the analyte sensor. The solvent chamber encapsulates a solvent. Example methods may also include coupling the porous medium to a feminine hygiene product. Some methods may include printing a surface of the display with information to facilitate interpretation of the visible indication.

Diagnostic assays with lateral flow, microfluidic, and/or flow-through formats for the detection of small molecules, target-specific antibodies, and other target analytes are known in the art. Such assays are used to detect one or more target analytes in a sample of blood, plasma, serum, extracellular fluid, and/or other body fluids. Various point-of-care assay kits in these formats are known and commercially available for use in monitoring parameters such as cholesterol, ferritin, c-reactive proteins, environmental toxins, viral infections, parasitic infections, bacterial infections, fungal infections, sexually transmitted diseases, drug testing/levels, vitamin/nutritional deficiencies, glucose levels, arthritis biomarkers, and a wide variety of other analytes/biomarkers.

Menstrual fluid is a source of blood that can be obtained non-invasively and without the assistance of medical personnel. Thus, analysis of menstrual fluid may be a discreet and user-accessible alternative to conventional blood screening. In accordance with the present disclosure, a menstrual fluid filtration article and/or analyte sensor may be configured for use on or within a feminine hygiene product.

In at least some aspects, a feminine hygiene product is provided with an integrated analyte sensor. This product can be worn by a user in the same manner as a conventional feminine hygiene product. The analyte sensor may include one or more of a sample collection matrix, a receptacle, a detection matrix, and a display. In some embodiments, menstrual fluid flowing into/onto the hygiene product enters the sample collection matrix, where cells and other particles are retained. The remaining liquid fraction flows into the receptacle. In some examples, cells (e.g., bacteria, yeast) may pass through the sample collection matrix in the liquid fraction and may be detected by the analyte sensor as whole organisms, as discussed in further detail below.

In some embodiments, an integrated analyte sensor may have a "sandwich" type assay format. In this format, a first detection reagent binds to target analytes in the liquid fraction, which flows from the sample collection matrix/receptacle into the detection matrix. Target analyte-first detection reagent complexes are optionally immobilized on the detection matrix by a second detection reagent (e.g., a capture reagent). An indicator bound to or associated with the first or second detection reagent provides a visible signal indicating the result of the assay, which may be viewed during use and/or as the product is being discarded. This format may be used, for example, to detect analytes with one or more antigenic sites, such as for example proteins and polysaccharides, and may be particularly effective with analytes having multiple antigenic sites, such as for example bacteria and viruses.

In other embodiments, an integrated analyte sensor may have a competitive assay format. In this format, the first detection reagent is a labeled complex that does not bind to the target analyte. A second detection reagent (i.e., a capture reagent) immobilized on the detection matrix captures either the target analyte, which is unlabeled, or the first detection reagent. In this example, the target analyte and the labeled complex are 'competing' for the second detection reagent; if no target analyte is present, the second detection reagent captures only the labeled first detection reagent. A third detection reagent immobilized downstream of the second detection reagent may be used to capture remaining first detection reagent. Therefore, the absence of a visible signal (or the presence of a relatively faint or weak signal) at the site of the second detection reagent and the presence of a signal at the site of the third detection reagent indicates the presence of the target analyte in the sample. The competitive assay format may be used, for example, to detect target analytes with relatively few antigenic sites and/or small molecules (e.g., mycotoxins, drugs). The competitive assay format and the sandwich assay format are merely two examples of assay formats suitable for use in an integrated sensor and are not intended to be limiting.

In still other embodiments, an integrated analyte sensor may have a non-antibody detection reagent, such as an aptamer and/or aptamer-modified nanoparticle. As used herein, an "aptamer" is an oligonucleotide (single-stranded DNA or RNA) or protein that binds with specificity to a target such as a protein, polysaccharide, ion, or small molecule. Aptamers may be used with one or more indicators that provide a visible color or color change. For example, aptamers may be used with one or indicators such as gold nanoparticles. Gold nanoparticles appear red in color when dispersed, and display a color shift toward blue as distance between the gold nanoparticles decreases. As is known in the art, gold nanoparticles tend to aggregate in salt solutions. This aggregation is reduced or prevented upon binding to single-stranded, but not double-stranded, nucleic acids. In addition, a nucleic acid aptamer may preferentially bind a target analyte, but may otherwise bind or remain bound to a complementary nucleic acid molecule. Therefore, aptamers and indicators may be used with a variety of assay formats to produce a visible color change that indicates the presence (or absence) of a target analyte.

Some analyte sensors may be provided with aptamers that are not coupled to indicators. For example, an analyte sensor may have an aptamer (i.e., the detection reagent) immobilized on the detection matrix in a spot or other pattern. Colored latex beads bound to single-stranded nucleic acids complementary to the aptamers may be provided upstream of the detection reagent, such as in the sample collection matrix. Similar to the above-described competitive assay format, the immobilized aptamers may bind the target analyte or the latex bead-DNA constructs. Thus, a visible color spot may indicate a negative result (i.e., that the target analyte is not present).

Alternatively, an analyte sensor may be provided with a detection reagent comprising aptamers that are adsorbed or covalently coupled to gold nanoparticles and to complementary nucleic acid strands. The double-stranded nucleic acids may allow aggregation of the aptamer-nanoparticle constructs. In the presence of a target analyte, the aptamers may bind the target analyte, releasing the complementary strands. The complementary strands may bind to the gold nanoparticles, resulting in an increase in negative charge and increased dispersion (i.e., color shift from blue toward red).

In some examples, the aptamer-nanoparticle constructs may be provided as aggregates, such as by coupling some or all of an aptamer to the gold nanoparticles of one group, coupling some or all of a complementary nucleic acid strand to the gold nanoparticles of another group, and adding the two groups to allow binding of the complementary strands to the aptamers. The resulting aggregation of the gold nanoparticles may cause them to appear blue in color. Binding of the aptamers to a target analyte may cause disassembly of the aggregates and release of the complementary strands, which may bind to the gold nanoparticles. This may allow dispersion of the nanoparticles, inducing a color shift toward red. In still other examples, aptamer-nanoparticle constructs provided as aggregates may be too large to pass through some portion of the analyte sensor (e.g., the detection matrix). Therefore, a faint or absent visible color signal on the detection matrix may indicate that the target analyte is absent, or is present at a low concentration. The aptamer-nanoparticle aggregates may be provided, for example, in the sample collection matrix, reservoir, detection matrix, or other analyte sensor component.

In some examples, some or all of the aptamers may be modified such that they are capable of binding to a capture reagent. The capture reagent may be immobilized in a spot, line, or other pattern. For example, some of the target-specific aptamers may be biotinylated, and the capture reagent may be or include streptavidin. The capture reagent may be added as a solution to the detection matrix and dried. Some analyte sensors may include a second detection reagent and a second capture reagent for use as a control and/or to provide an indication of non-target analyte concentration. The result of the assay may then be read on a sliding scale based at least in part on the control indication. For example, an aptamer-nanoparticle construct that binds to albumin may be included to provide an indication of the concentration of serum/plasma/menstrual fluid in the liquid received by the analyte sensor. The analyte sensor may be further provided with a sliding scale that is adjusted by the user based on the color/intensity of the control and is then used to determine the concentration of the target analyte. Alternatively, a control may be provided to indicate that the assay is working, and the result of the assay for the target analyte may be determined without further reference to the control.

Unless indicated otherwise, all technical and scientific terms used herein have the same meaning as commonly understood by one of ordinary skill in the art. Unless otherwise noted, conventional methods and materials are used for manufacturing the articles described, such as those provided in the art and in general references. Terms of orientation such as "up" and "down" or "upper" or "lower" or "upstream" and "downstream" and the like refer to orientation of the parts during use of the article. As employed throughout the disclosure, the following terms, unless otherwise indicated, shall be understood to have the following meanings:

As used herein, "menstrual fluid" can include uterine tissues, blood, extracellular fluids, mucus, secretions, glandular tissue of the endometrium, and/or any other biological materials discharged from the female reproductive tract. Likewise, "menstruation" can refer to any discharge of blood/menstrual fluid from the female reproductive tract at any time and during any phase of the menstrual cycle. Blood may further include but is not limited to cells (e.g., erythrocytes, leukocytes, thrombocytes, etc.), water, serum, plasma, cholesterol, triglycerides, clotting factors, glucose, amino acids, lipids, fatty acids, lipoproteins, serum albumin, sodium, chloride, urea, uric acid, lactic acid, vitamins, minerals, hormones, antibodies, plasma proteins, fibrin, fibrinogen, carbohydrates, iron, oxygen, carbon dioxide, bicarbonate ions, and/or nitrogen.

As used herein, a "liquid component of menstrual fluid" can include serum, plasma, extracellular fluids, liquid secretions, and/or any other liquid component of menstrual fluid in any combination. As used herein, "menstrual fluid particles" can include any solid or semi-solid component of menstrual fluid, such as tissue, mucous, mammalian cells (e.g., erythrocytes, leukocytes, etc.), and non-mammalian cells (e.g., protozoa, bacteria, yeast, fungi). "Tissue," as used herein, means a group (i.e. two or more) of mammalian cells physically coupled together. Examples of tissue include, but are not limited to, endometrial tissue, glandular tissue, and coagulated blood components (e.g., cells embedded within a fibrin matrix).

As used herein, a "feminine hygiene product" can be any article configured to collect menstrual fluid from within the female reproductive tract (e.g., a tampon, a menstrual cup, etc.) or externally (e.g., a menstrual pad). A "menstrual pad" can be any article configured to be retained in the path of a flow of menstrual fluid exiting the female reproductive tract. Examples of menstrual pads include, but are not limited to, sanitary pads, sanitary napkins, and pantiliners. Menstrual cups are known in the art and commercially available, and examples are generally described in U.S. Pat. No. 2,534,900 to Chalmers, incorporated by reference herein. In some examples, a feminine hygiene product may include an integrated analyte sensor and may have a total thickness of 75 µm or more (e.g., 75-100 µm, 100-500 µm, 500-1000 µm, 1-10 mm, 10-100 mm, 100 mm-5000 mm).

As used herein, a "prefilter" is a porous fabric, mesh, weave, web, pad, membrane, film, or sheet positioned upstream of a sample collection matrix. A prefilter may include one or more polymers, polyurethane particles, a porous foam, a reticulated foam, natural/synthetic fibers (e.g., wood, cotton, polyester, polypropylene, cotton, cellulose). Examples of prefilters include top sheets/layers of commercially available sanitary napkins. A prefilter may have pores connecting the upper and lower surfaces of the prefilter, and the pores may be sized to block passage of tissues and/or viscous mucus while allowing fluids to pass. In some examples, a prefilter may be a sheet of a polymeric web with conical or tapering pores that are larger in diameter on the upper surface and smaller in diameter on the lower surface. Examples of such polymeric webs are described in the following references, which are incorporated by reference herein: U.S. Pat. No. 3,929,135 to Thompson; U.S. Pat. No. 4,342,314 to Radel and Thompson; U.S. Pat. No. 4,609,518 to Curro et. al.; and U.S. Pat. No. 4,629,643 to Curro and Linman.

Prefilter pores may have diameters in the ranges of, for example, 5-10 µm, 10-50 µm, 10-100 µm, 100 µm to 500 µm, or 500 µm to 5000 µm. The thickness of a prefilter may be in the range of 50-500 µm, 100-500 µm, 500 µm-1000 µm, or 1 mm-10 mm.

Optionally, a prefilter may be treated with one or more agglutinants. As used herein, an "agglutinant" can include a coagulant or any other substance that promotes the adhesion of particles (e.g., erythrocytes). Agglutinants can include lectins and/or antibodies. Examples of agglutinants for erythrocytes include anti-erythrocyte antibodies, concanavalin A, wheat germ agglutinin, soybean agglutinins, and other commercially available lectins.

As used herein, a "sample collection matrix" is a porous, liquid-permeable sheet, pad, membrane, fabric, mesh, weave, or web configured to allow passage of a liquid. A sample collection matrix can be constructed of any natural or synthetic material, including (but not limited to) glass fibers, glass microfibers, polyester staple fibers, polyester binder fibers, polysaccharides, cellulose esters, nitrocellulose, cellulose acetate, cellulose nitrate, polyvinylidene fluoride (PVDF), polyethylene, nylon, rayon, polyester, polyethersulfone (PES), polysulfone, vinyl, vinyl chloride, vinyl chloride-propylene copolymer, vinyl chloride-vinyl acetate copolymer, nitrile, nylon, polypropylene, polytetra-fluoroethylene (PTFE), cotton, cotton linter paper, polyacrylamide, and/or polyvinylidene fluoride. A sample collection matrix may be a non-woven (e.g., wet laid, spunbond, spun lace, spun cast, melt blown) or a woven material. Examples of sample collection matrices include, but are not limited to, glass microfiber filters (Whatman, Kent, UK or Millipore), PlasmaSep® (Whatman) and C/S membranes, C/Q membranes, and S/G membranes (Spectral Diagnostics).

A sample collection matrix can be, or can include as a separate component, one or more membranes and/or filters configured to exclude components of a collected fluid sample (e.g., erythrocytes) on the basis of size. In at least some examples, the sample collection matrix includes an asymmetric membrane. As used herein, an "asymmetric membrane" is a membrane with pores that decrease in diameter between a first surface (i.e. top/upper/upstream) and a second surface (i.e. bottom/lower/downstream). As liquid flows laterally from the first surface to the second surface, particles are trapped within the narrowing pores. An asymmetric membrane may have an upstream:downstream pore diameter ratio of 5:1, 8:1, 10:1, 50:1, 100:1, etc. In some examples, an asymmetric membrane may have an upstream:downstream pore diameter ratio within the ranges of 5-10:1, 10-100:1, or 20-200:1. Pore diameters on the upstream (i.e. top/upper) surface of the asymmetric membrane may be within the ranges of 1-10 µm, 5-50 µm, 10-100 µm, 20-200 µm, 50-500 µm, or 100-1000 µm. Pore diameters on the downstream surface of the asymmetric membrane may be within the ranges of 0.001-0.01 µm, 0.005-0.05 µm, 0.01-0.1 µm, 0.05-0.5 µm, 0.1-1 µm, or 0.5-5 µm. Examples of asymmetric membranes are the Asymmetric Super Micron Polysulfone (MMM), Highly Asymmetric Sub-micron Polysulfone (BTS), and Asymmetric Polyethersulfone (Supor®) membranes, all manufactured by Pall Corporation. One example of an asymmetric membrane suitable for filtration of erythrocytes from blood is the BTS-SP-300 membrane (Pall, Inc.).

Alternatively, a sample collection matrix may be two, three, or more symmetric or asymmetric porous membranes vertically stacked according to pore size. For example, a membrane with an average pore diameter in the range of 0.1-100 µm may be positioned below a membrane with a larger average pore diameter (e.g., 10-1000 µm) and above another membrane with a smaller average pore diameter (e.g., 0.001-0.1 µm).

The dimensions and thickness of a sample collection matrix may vary among examples. In some examples, the sample collection matrix may be a symmetric or asymmetric membrane with a thickness in the range of 50-500 µm. In other examples, the sample collection matrix may be an asymmetric membrane with a thickness in the range of 100-300 µm. In still other examples, the sample collection matrix may be a membrane, pad, or stack with a thickness in the range of 100 µm-1000 µm or in the range of 1 mm-30 mm. The thickness and pore sizes of the sample collection matrix and/or other components of the analyte sensor may be selected based on the desired flow rate (i.e., volume per unit of time) and the size of the cells/particles to be filtered. For example, flow rate may be decreased by using materials that are thinner (e.g., in a lateral flow format), thicker (e.g., in a flow-through format), and/or have smaller pores. For example, in lateral flow format applications where slower flow through the sample collection matrix is desirable, the sample collection matrix may be relatively thin (e.g., 40-80 µm thick) and/or have relatively small pores (e.g., 0.1-2 µm). In other lateral flow format applications, a thicker (e.g., 80-150 µm thick) sample collection matrix may be provided to increase flow rate and/or accommodate a larger sample volume.

As used herein, "receptacle" refers to an article that is configured to receive and retain a filtered sample fluid from a sample collection matrix. A receptacle can be hollow, porous, and/or liquid-permeable and may include one or more natural or synthetic materials, including (but not limited to) polysaccharides, cellulose esters, nitrocellulose, cellulose acetate, cellulose nitrate, polyvinylidene fluoride (PVDF), polyethylene, nylon, rayon, polyester, polyethersulfone (PES), polysulfone, vinyl, vinyl chloride, vinyl chloride-propylene copolymer, vinyl chloride-vinyl acetate copolymer, nitrile, nylon, polypropylene, polytetra-fluoroethylene (PTFE), cotton, cotton linter paper, polyacrylamide, and/or polyvinylidene fluoride.

A hollow receptacle can be a tube or roll of porous material with an interior void. Alternatively, a hollow receptacle can be a channel, trough, cutout, or other void designed to retain a volume of sample fluid. For example, a hollow receptacle can be a gap or space between a sample collection matrix and a detection matrix. Liquid may flow from the sample collection pad into the hollow receptacle by capillary action and may then flow into the detection matrix. Alternatively, a hollow receptacle can be a channel or groove formed in a membrane or stack of membranes or machined/laser-cut into a solid support. Examples of such receptacles are described in U.S. Patent App. Pub. No. 2006/0246600 to Yang et al., incorporated by reference herein.

A porous receptacle can be a pad, membrane, or stack of pads/membranes. In some examples, no receptacle is provided. In other examples, the sample collection matrix and receptacle may be a single component, such as an asymmetric polyethersulfone/polysulfone membrane (e.g., BTS-SP-300 membrane, Pall Inc.). Alternatively, a porous receptacle may be one or more layers of a porous substance, such as a folded nitrocellulose membrane or a pad constructed of a natural fiber such as cotton. In at least some examples, a porous receptacle may be a compressed or pleated absorbent material (e.g., a pad of dried, compressed cellulosic material) or foam that is configured to expand as it absorbs filtered sample fluid from the sample collection matrix. The expansion of the receptacle may place the receptacle into capillary contact with a detection matrix, allowing analyte detection to be delayed until a desired volume of sample fluid has been received by the receptacle. An example of an expandable sample pad is described in U.S. Pat. No. 5,985,675 to Charm et al., which is incorporated by reference herein.

The dimensions and thickness of a receptacle may vary among examples. In some examples, the receptacle may be a membrane with a thickness in the range of 50-500 µm. In other examples, the receptacle may be an asymmetric membrane with a thickness in the range of 100-300 µm. In still other examples, the receptacle may be a membrane, pad, or stack with a thickness in the range of 100 µm-1000 µm or in the range of 1 mm-10 mm. As described above, materials for the receptacle may be selected based on factors such as thickness, pore size(s), and desired flow rate.

A "stack" can be a vertical arrangement of layers (e.g., a prefilter, sample collection matrix, and/or receptacle) in which one layer is placed onto another. For example, a prefilter can be placed onto a sample collection matrix. Layers of a stack may be coupled by heating, melting, laminating, gluing, ultrasonic bonding, welding, or crushing/compressing the outer edges of two or more layers. In one example, the outer periphery of a stack may be sealed with hotmelt-coated aluminum foil seals as described by Law (1997). In other examples, layers may be coupled by applying an adhesive, sealant, or a hydrophobic substance to the outer edges of the layers and/or between the layers. One or more layers of a stack may be removably coupled to another layer of the stack. For example, a bonded prefilter and sample collection matrix can be placed onto a receptacle without bonding the receptacle. Alternatively, the receptacle can be coupled to the other layers with a removable adhesive such as an adhesive tape.

As used herein, a "detection matrix" can be a membrane or other porous material that includes a detection reagent (e.g., a capture reagent) and/or indicator immobilized on one or more surfaces. A detection matrix can be constructed of any natural or synthetic material, including (but not limited to) polysaccharides, cellulose esters, nitrocellulose, cellulose acetate, cellulose nitrate, polyvinylidene fluoride (PVDF), polyethylene, nylon, rayon, polyester, polyethersulfone (PES), polysulfone, vinyl, vinyl chloride, vinyl chloride-propylene copolymer, vinyl chloride-vinyl acetate copolymer, nitrile, nylon, polypropylene, polytetra-fluoroethylene (PTFE), cotton, polyacrylamide, and/or polyvinylidene fluoride.

Alternatively, a "detection matrix" can be a non-porous plastic or polymer material having one or more surface-bound detection reagents. For example, a detection matrix can be a flat strip of plastic with one or more surface-bound antibodies specific to a target analyte. The strip can be positioned below a sample collection matrix or filter to capture and retain the target analyte without retaining the fluid (e.g., a flow-through assay). Alternatively, the strip can be positioned in a portion of a feminine hygiene product that does not receive a flow of fluid, and filtered fluid within a receptacle can be applied to the strip in a separate process after the feminine hygiene product has been used.

In some examples, the sample collection matrix, detection matrix, and/or reservoir may be a continuous strip or sheet of material. In other examples, one or more of these components may be separate strips or sheets of material. As described above, the detection matrix may be positioned such that it is not in fluid communication with the sample collection matrix/reservoir while menstrual fluid is being collected. Some analyte sensors may lack a reservoir and/or a sample collection matrix.

A detection matrix may be provided with a plurality of surface-bound detection reagents and/or capture reagents. In some examples, a detection matrix may be provided with a plurality of different detection/capture reagents immobilized in one or more shapes such as, but not limited to, squares, dots, lines, symbols (e.g., "+"), or numbers/letters. The shapes may be arranged on/in the detection matrix in rows and/or columns to form an array. For example, a detection matrix may be provided with twenty detection/capture reagents. Each of the twenty detection/capture reagents may be specific to a different target analyte and may be immobilized as a separate dot. In other examples, a detection matrix may be provided with any suitable number of detection/capture reagents, such as 2-10, 5-25, 10-40, 20-50, 25-100, or 100-10,000 detection/capture reagents.

The dimensions and thickness of a detection matrix may vary among examples, as described above with regard to the sample collection matrix and receptacle. In some examples, the detection matrix may be a symmetric or asymmetric membrane with a thickness in the range of 50-500 µm. In other examples, the detection matrix may be an asymmetric membrane with a thickness in the range of 100-300 µm. In still other examples, the detection matrix may be a membrane, pad, or stack with a thickness in the range of 100 µm-1000 µm or in the range of 1 mm-10 mm.

A prefilter, sample collection matrix, receptacle and/or detection matrix may be treated with a wetting agent, such as a surfactant (e.g., glycerol, Tween, Triton X-100). Examples of wetting agents are described in U.S. Patent App. Pub. No. 2006/0246600 to Yang et al. and U.S. Patent App. Pub. No. 2009/0142229 A1 to MacDonald and Smith, incorporated by reference herein.

A lysis buffer may be provided on or within the sample collection matrix and/or prefilter to lyse cells and release a target analyte, such as a protein, a glycoprotein, a proteoglycan, a nucleic acid (e.g., DNA, RNA), and/or a lipoprotein. Lysis buffers are known in the art and may include, for example, salts (e.g., ammonium chloride, sodium chloride, potassium chloride), amphoteric agents (e.g., Lyso PC, CHAPS, Zwittergent), cationic agents (e.g., C16 TAB, benzalkonium chloride, ionic detergents (e.g., SDS, cholate, deoxycholate), non-ionic detergents (octylglucoside, Digitonin, C12E8, Lubrol, Triton X-100, Noniodet P-40, Tween 20, Tween 80), a preservative (e.g., sodium azide), and/or other components such as sodium hydroxide, bovine serum albumin, urea, enzymes, and/or EDTA. The lysis buffer may be added to the sample collection matrix as a liquid and subsequently dried. Similarly, a neutralizing reagent may be added to the reservoir as a liquid and subsequently dried. The lysis buffer may lyse cells within the menstrual fluid as the menstrual fluid flows into the sample collection matrix. When the fluid dissolves the neutralizing reagent, the neutralizing reagent may alter one or more characteristics of the fluid. For example, the neutralizing reagent may raise (or lower) the pH of the fluid to a pH within the range of 6.8-7.8.

As used herein, a "display" can be a sheet of paper, plastic, polymer, elastomer, or deformable material configured for displaying an assay result. For example, a display can be a sheet of plastic with an aperture or other void through which a detection matrix of an analyte sensor can be viewed. A display may be printed or marked with information to aid interpretation of the results, such as a calibration scale, labels, or instructions relating to the assay. A display may be coupled to an analyte sensor and/or feminine hygiene product with by melting, crushing/compressing, laminating, welding, and/or applying an adhesive. In some examples, the display may be permanently coupled to a detection matrix (e.g., with an adhesive) and removably coupled to a lower portion of the analyte sensor/hygiene product (e.g., with a removable tape). The display and detection matrix may be peeled from the analyte sensor/hygiene product as a single unit to provide a record of the assay result.

As used herein, a "positioning element" is an adhesive, fastener, seal, absorbent material, cord/tie, or other element configured to retain a sample collection matrix in the path of a flow of menstrual fluid. Two, three, or more than three positioning elements may be used in any combination. Examples of positioning elements may include but are not limited to an outer absorbent layer of a tampon (see e.g., FIG. 2, positioning element 204), an adhesive tape (see e.g., FIG. 3b, positioning element 330), a sanitary napkin holder (see e.g., FIG. 3a, holder 350), and an absorbent pad at least partially surrounding the sample collection matrix (see e.g., FIG. 3a-3b, overflow pad 324).

As used herein, an "analyte sensor" can be any apparatus/article configured to detect and indicate the presence or absence of an analyte in a sample of menstrual fluid, in a liquid component of menstrual fluid, and/or in an isolated fraction of menstrual fluid. An analyte sensor may include one or more of a sample collection matrix, a receptacle, a detection matrix, a detection reagent, a capture reagent, and/or a display. Menstrual fluid and/or a liquid component of menstrual fluid may be moved among components of an analyte sensor via capillary action, pressure, suction, osmosis, diffusion, and/or gravitational force. Examples of analyte sensors for detection of analytes in body fluids are described in the following references, which are incorporated by reference herein: Law et al., *Clinical Chemistry* 43(2), (1997): 384-389; Allen et al., *Clinical Chemistry* 36(9), (1990): 1591-1597; U.S. Pat. No. 5,468,236 to Everhart et al.; U.S. Pat. No. 6,713,660 to Roe et al.; U.S. Patent App. Pub. No. 2006/0246600 to Yang et al.; U.S. Patent App. Pub. No. 2010/0015658 to Yang et al.; U.S. Patent App. Pub. No. 2009/0142229 to MacDonald and Smith; U.S. Patent App. Pub. No. 2010/0089815 to Zhang et al.; U.S. Pat. No. 7,605,004 to Zhou; and WO 2004/092342 A2 to Gerdes et al.

In addition, absorbent pads with integrated biosensors have been described in the following references, which are incorporated by reference herein: U.S. Pat. No. 6,186,991 to Roe et. al.; U.S. Pat. No. 6,713,660 to Roe and Muscat; U.S. Patent App. Pub. No. 2004/0172000 A1 to Roe and Muscat; U.S. Pat. No. 5,468,236 to Everhart et al.; and U.S. Pat. No. 6,921,647 to Kritzman et al.

As used herein, a "detection reagent" can be or include any substance that binds to, or interacts chemically with, a target analyte or its product, another detection reagent, and/or an indicator. A "capture reagent" can be or include any detection reagent or other substance that binds with specificity to a target analyte, a product of a target analyte, or another detection reagent, and which is immobilized (e.g., on or in a detection matrix). Examples of target analytes include, but are not limited to, proteins, glycoproteins, proteoglycans, nucleic acids, and lipoproteins. Detection reagents and capture reagents may include, but are not limited to, one or more of the following in any combination: an antibody, an enzyme, coenzymes, an antibody-enzyme complex, an aptamer, a nanoparticle, a nucleic acid, an oligonucleotide, a dye (e.g., fluorescent, phosphorescent, chemiluminescent, crystalites, etc.), a particle (e.g., a colored latex particle, a magnetic particle, a colored carboxyl-polystyrene particle, etc.), a colloidal particle (e.g., gold, silver, selenium, etc.), a platinum particle, a metal chelate, an electroactive group, a stable radical, etc. A "detection reagent" can also include any substance that competes with the target analyte or its product in interactions with another ligand/molecule (e.g., a competitive binding inhibitor). One or more components of a detection reagent or capture reagent may be coupled to an enzyme such as cholesterol esterase, cholesterol oxidase, or a peroxidase (e.g., horseradish peroxidase, soybean peroxidase), and/or to an indicator (see next).

An "indicator" can include any substance that is designed to provide a visible signal of analyte detection. In some examples, and indicator may be a visible and/or colloidal particle, such as a gold or colored latex particle. An "indicator" can also be an enzyme, an enzyme substrate, and/or any substance that is altered/activated by a detection reagent, by an analyte, or by a product of an analyte, to produce a visible signal. Examples of indicators include but are not limited to a pH indicator, a dye, a fluorophore, a colloidal platinum particle, and an enzyme substrate that interacts with an enzyme to produce a colored precipitate.

An indicator may be a component of a detection reagent or capture reagent. In one example, a detection reagent is a gold colloidal particle coupled to an antibody specific for a target analyte, and the gold colloidal particle is an "indicator." Alternatively, an indicator may be provided separately from the detection/capture reagent. For example, a dye designed to produce a visible color upon wetting may be provided in an anhydrous form on the end of a lateral flow strip, a display, or other component of an analyte sensor to indicate that detection has been completed.

An analyte sensor may be configured to convey the presence or absence of a target analyte as either a "positive" or a "negative" result. Analyte sensors may generate a visible signal, such as a collection of colored particles on a surface, to indicate that the analyte was detected in the tested sample. An analyte sensor may generate such a signal in response to detection of the analyte at any concentration above a minimum threshold concentration. For example, an analyte sensor may produce a color deposit in response to the detection of triglycerides at any concentration equal to or greater than 150 mg/dL. Alternatively, an analyte sensor may generate a "positive" signal in response to detection of the analyte at any concentration, without a minimum threshold. For example, an analyte sensor may produce a color deposit in response to the detection of a toxin at any concentration.

Some analyte sensors may further indicate the presence of the analyte in a quantitative manner corresponding to the concentration of the analyte in the sample. A quantitative signal may be proportional to the concentration of the target analyte (e.g., a noncompetitive immunoassay) or inversely proportional to the concentration of the target analyte (e.g., a competitive immunoassay). For example, an analyte sensor may produce a color deposit of varying intensity (e.g., light blue to dark blue), a variation in the deposited color (e.g., yellow to red), and/or a colored deposit of varying size/length/dimensions (e.g., a colored bar of variable length) in response to varying analyte concentration. An analyte sensor may detect an analyte with an antibody or indicator substance (e.g., a dye, an enzyme, etc.) that binds to or is chemically altered by the analyte itself. An analyte sensor may also/instead detect a product of the analyte (e.g., a cleavage product, a product of a chemical reaction involving the analyte, etc.).

Analyte sensors may be arranged in various formats, such as flow-through and lateral flow formats and/or combinations thereof. In one example of a lateral flow format, the analyte sensor includes a detection matrix in the form of a strip of chromatographic material (e.g., nitrocellulose-coated Mylar). The strip is coupled at a first end to a sample collection matrix/reservoir containing a first detection reagent, such as target analyte-specific antibodies coupled to colloidal gold or colored latex particles. A second detection reagent, such as an antibody specific to a different epitope of the target analyte, is immobilized on the strip in a spot, stripe, or other shape. A capture reagent, such as an antibody to a component of the first detection reagent, is also immobilized on the strip downstream of the second detection reagent. Finally, the opposite end of the strip is coupled to an absorbent material designed to enhance capillary flow of liquids through the strip and prevent fluid backflow through the strip.

In this example, menstrual fluid flows into the sample collection matrix which removes particulates such as erythrocytes and yeast cells from the menstrual fluid. The filtered fluid flows by capillary action from the sample collection matrix into a reservoir, where the first detection reagent mixes with the fluid and binds target analytes. The first detection reagent may be supplied in the reservoir as a powder. For example, the first detection reagent may be added onto/into the reservoir in a liquid medium (e.g., water or buffer) and the reservoir may be dried. When the filtered fluid flows into the reservoir, the first detection reagent is rehydrated and dissolved to form a mixed fluid.

The mixed fluid contacts the detection matrix and is drawn through it by capillary action, passing first through the deposit of immobilized second detection reagent. The target analyte binds to the second detection reagent and is thereby immobilized. The first detection reagent bound to the target analyte is also immobilized, with the gold/latex particles forming a visible colored spot or line at the site. Remaining first detection reagent that is not bound to target analyte molecules flows past the second detection reagent to be captured and immobilized by the capture reagent. This results in a second line or spot that indicates completion of the assay.

In another example of a lateral flow format, the analyte sensor is arranged as a nucleic acid lateral flow assay/microarray. Nucleic acid lateral flow assays and microarrays are known in the art. Nucleic acid lateral flow assays are described, for example, in Carter and Cary, *Nucleic Acids Research*, 35 (10), pub. online May 3 (2007): e74 pp 1-11. Nucleic acid lateral flow microarrays are described, for example, in WO 2004/092342 A2 to Gerdes et al. These documents are incorporated by reference herein. In some examples, an analyte sensor arranged as a nucleic acid lateral flow assay may include a sample collection matrix/reservoir and a detection matrix. A lysis buffer may be provided in the sample collection matrix or in a prefilter, as described above, to lyse cells and release RNA/DNA. The reservoir may be provided with a neutralizing reagent, a first set of oligonucleotide proves coupled to a first detection reagent, and a second set of oligonucleotide probes coupled to a second detection reagent. A third detection reagent may be reversibly immobilized (e.g., spotted and dried) in the detection matrix. The third detection reagent may be configured to bind to the first detection reagent, and may be coupled to a marker such as a gold or latex particle. A capture reagent configured to bind the second detection reagent may be immobilized on the detection matrix downstream of the third detection reagent.

Menstrual fluid with cells may flow into the sample collection matrix and/or prefilter, dissolving the lysis buffer to form a mixed fluid. The lysis buffer may cause the cells to release RNA/DNA. The mixed fluid may flow from the sample collection matrix to the reservoir and may dissolve the neutralizing agent and the first and second sets of oligonucleotides. The first and second sets of oligonucleotides may bind to the target RNA/DNA sequences to form reagent-target complexes. The mixed fluid with the reagent-target complexes may then flow from the reservoir to the detection matrix. When the mixed fluid reaches the third detection reagent, the third detection reagent may bind the first detection reagent. Subsequently, as the mixed fluid continues to flow through the detection matrix, the capture reagent may bind the second detection reagent. Reagent-target complexes that include each of the first, second, and third detection reagents are immobilized by the capture reagent on the detection matrix and form a visible signal (e.g., a spot or line) to indicate a positive result.

Analyte sensors having a flow-through format may include a sample collection matrix positioned above a detection matrix. Optionally, a receptacle may be positioned between the sample collection matrix and the detection matrix. A labeled first detection reagent is provided within the sample collection matrix/reservoir. A second detection reagent and/or a capture reagent is immobilized on or in the detection matrix. Menstrual fluid flows downward through the sample collection matrix, which filters cells and tissue from the fluid. The remaining fluid mixes with the first detection reagent as it flows downward onto the detection matrix. Target analytes are immobilized by the second detection reagent and/or capture reagent as described above. In some examples, another detection/capture reagent captures unbound first detection reagent. The detection matrix is then viewed to obtain the results of the assay.

In one example, an analyte sensor with a flow-through format is configured to detect an allergy to one or more allergens. A first detection reagent is provided in the sample collection matrix or reservoir. The first detection reagent is an antibody to IgE that is coupled to an indicator such as a colored latex particle. A second detection reagent (e.g., a capture reagent) is immobilized on the detection matrix. The second detection reagent is an allergen (e.g., casein). As menstrual fluid flows into the sample collection matrix/reservoir, the first detection reagent binds to IgE in the menstrual fluid and forms reagent-IgE complexes. The menstrual fluid continues to flow downward and into the detection matrix. If the IgE of the labeled reagent-IgE complexes bind to the second detection reagent, a color deposit forms and indicates a positive result (i.e., an allergy to casein). The detection matrix may have any number of immobilized detection/capture reagents in order to evaluate a range of allergens simultaneously.

Some analyte sensors may have a combination of vertical and lateral flow formats. For example, a sample collection matrix may be positioned vertically above and in fluid communication with a detection matrix. Menstrual fluid may flow downward through the sample collection matrix, which may filter particles from the menstrual fluid. The filtered fluid may flow into, and laterally through, the detection matrix as described above.

Multiple detection reagents, capture reagents, and/or indicators may be provided on or within one or more components of an analyte sensor. In some examples, detection reagents may include two or more antibodies specific to separate epitopes of the same target analyte (e.g., sandwich assay format for detection of target protein(s)). Alternatively, detection reagents for detecting target proteins may include a first antibody specific to an epitope of a target analyte and a second antibody specific to the first antibody and/or a molecule coupled to the first antibody. In other examples, a first detection reagent may be a labeled complex that does not bind to the target analyte and a second detection reagent may include an antibody or other molecule that can bind either the unlabelled target analyte or the first detection reagent (e.g., a competitive assay format for detecting target proteins). In still other examples, detection reagents for the detection of nucleic acid targets may include nucleic acids or nucleic acid conjugates, as described above.

In accordance with one aspect, a menstrual fluid filtration article may be provided for use on or within a conventional feminine hygiene product, such as a menstrual pad or menstrual cup. The article may include a sample collection matrix (i.e., a porous matrix) configured to filter a flow of menstrual fluid in situ. Optionally, the article may further include a receptacle coupled to the sample collection matrix. The sample collection matrix may receive a flow of menstrual fluid and retain particulate component (e.g., erythrocytes and/or other solids/particles) on the basis of size, while allowing passage of the liquid component (e.g., plasma, serum, extracellular fluid). The liquid component may be drawn by capillary action from the sample collection matrix into the receptacle. The receptacle/article may then be removed from the hygiene product, and the liquid component within the receptacle may be used in an assay to detect a target analyte in the filtered fluid.

In other aspects, an analyte sensor may be provided for use with a pre-existing feminine hygiene product. Alternatively, an analyte sensor may be integrated within a feminine hygiene product (e.g., a menstrual pad, tampon, or menstrual cup). The analyte sensor may include a sample collection matrix and a receptacle as described above, a detection matrix with one or more detection reagents and/or indicators, and a display surface with a printed incremental scale or labels to facilitate user interpretation of the assay results.

Menstrual fluid may be received and filtered by the filtration article. The filtered fluid may be drawn from the reservoir to the detection matrix by capillary action and/or gravity. The detection matrix may include one or more detection reagents and/or indicators designed to provide a visual indication of the presence/concentration of a target analyte. The display surface may be provided with printed information, such as a calibration scale, numbers, labels, instructions, or other guidelines for user interpretation of the result.

FIG. 1 illustrates a block diagram of an illustrative embodiment of a disposable article for filtration of menstrual fluid in situ. As illustrated, a disposable article for filtration of menstrual fluid in situ may include prefilter 102, sample collection matrix 104, and receptacle 106, all arranged as a vertical stack. Sample collection matrix 104 may be a porous matrix that is coupled to prefilter 102 and receptacle 106 by various methods as described above. In some examples, the layers may be positioned within a non-porous sleeve or base that extends upwardly along the vertical sides of the stack (see e.g., FIG. 5a, sample chamber 562) and sealed to the sleeve/base with an adhesive.

Prefilter 102 and sample collection matrix 104 may be coupled to receptacle 106 in a single unit configured for use with a standard menstrual pad, such as a sanitary napkin. In one such example, prefilter 102, sample collection matrix 104 and receptacle 106 may be flat, elongate membranes measuring 5-20 mm in width and 30-100 mm in length, and vertically stacked and sealed together at the outer edges as described above. The stack may be laminated to a solid support, such as a flexible rubber or plastic strip of approximately the same dimensions. An adhesive tape or other fastener may be provided on the bottom of the solid support.

An anhydrous detection reagent, such as an antibody-indicator complex, may be provided within the sample collection matrix or between the sample collection matrix and the receptacle. The receptacle may be provided with capture reagent(s) immobilized on its bottom surface. The stack may be adhered onto an upper surface of the sanitary napkin with the adhesive tape, and the sanitary napkin may then be worn in the conventional manner.

As menstrual fluid flows onto the filter, the prefilter and sample collection matrix may remove erythrocytes, mucus, and cells/tissue from the fluid. The filtered fluid may mix with the detection reagent and flow downward into the receptacle by capillary action. Analyte-detection reagent complexes may be immobilized on the underside of the receptacle by the capture reagent. Excess filtered fluid may flow into the sanitary napkin below the receptacle. When the user is ready to discard the sanitary napkin, the filter and receptacle can be removed to view the assay result on the bottom surface of the receptacle. Prefilter 102 may be provided with relatively large and/or conical pores, as described above, to retain mucous and tissue.

Sample collection matrix 104 may be selectively permeable to particles, such as mammalian erythrocytes, on the basis of particle size. Sample collection matrix 104 may remove particles from menstrual fluid received from prefilter 102, allowing a fluid component of the menstrual fluid to pass through sample collection matrix 104.

Some embodiments may optionally lack a prefilter. For example, a menstrual fluid filtration article designed for use with a menstrual cup may include a sample collection matrix that is a circular microporous membrane or membrane stack. For example, the sample collection matrix may be a round BTS-SP-300 membrane with a diameter of 1-3 inches. The sample collection matrix may be continuously sealed around its outer edge to the rim of a concave, transparent, non-porous polymer support 1-3 inches in diameter and 0.1-1.0 inches in height by heating, melting, or with an adhesive. The interior void within the support may function as a receptacle.

The interior surface of the support may be coated with a wetting agent. Alternatively, the interior surface of the support may have a series of microchannels, grooves, or other surface texture configured channel fluids from the sample collection matrix onto the interior surface of the support. As menstrual fluid flows into the menstrual cup, erythrocytes and other particulates are retained above or within the sample collection matrix while the filtered fluid component flows downward along the inner surfaces of the support to collect at the bottom. Optionally, a porous membrane or fibers/particles may be provided in the receptacle to increase flow by capillary action.

Optionally, a first detection reagent may be provided in anhydrous form along the vertical inner surfaces of the support and/or in the receptacle. A second detection reagent and/or capture reagent may be immobilized on the interior surface of the support (e.g., near or at the bottom). As the filtered fluid mixes with the first detection reagent and flows to the bottom of the receptacle, the capture reagents may bind target analytes and/or unbound first detection reagent as described above.

In use, the menstrual fluid filtration article may be inserted into a conventional menstrual cup. The menstrual cup may subsequently be inserted into a body and used in the conventional manner. When the menstrual cup is removed and emptied, the menstrual fluid filtration article may be removed and the result of the analyte detection may be viewed through the transparent bottom surface of the support. The menstrual fluid filtration article may be provided in various sizes corresponding to commercially available menstrual cups and diaphragms. In one example, the menstrual fluid filtration article may have a diameter of between 50 and 95 mm for use with a diaphragm, and may be provided with detection reagents for detecting one or more cervical cancer markers.

Figure 2:
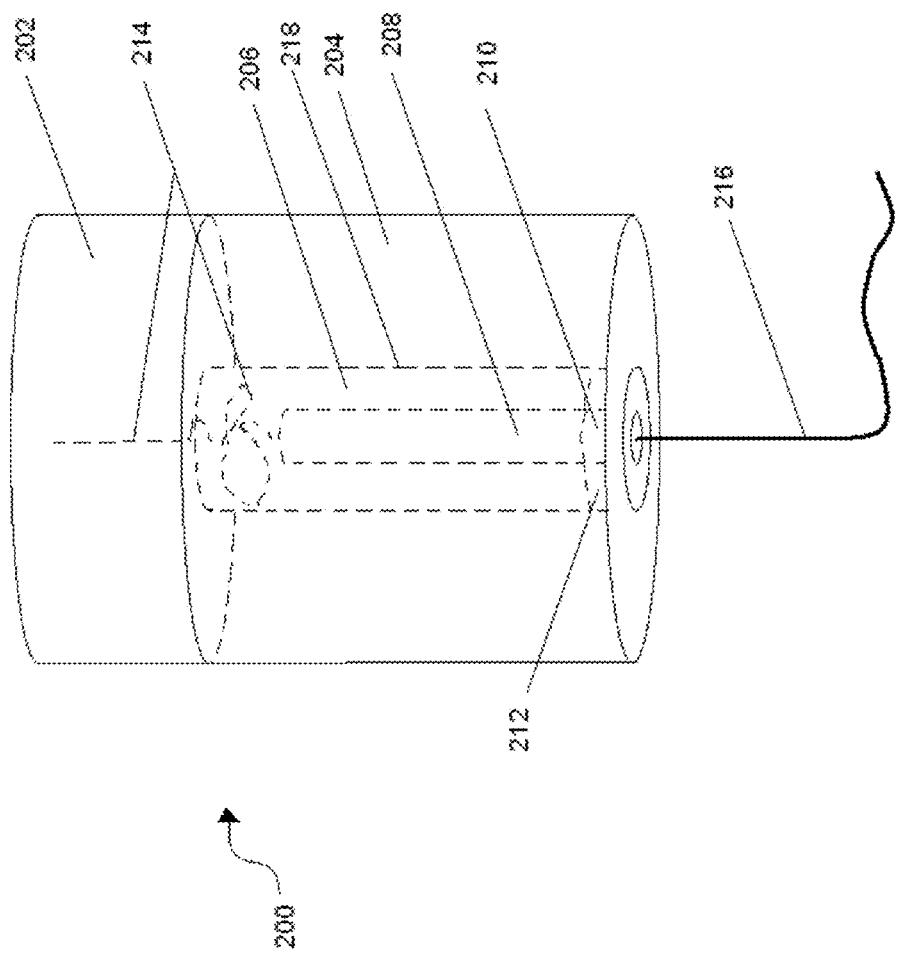
FIG. 2 illustrates a schematic of an illustrative embodiment of a disposable article for filtration of menstrual fluid in situ.

A sample collection matrix and receptacle may be supplied pre-integrated within a feminine hygiene product. For example, FIG. 2 illustrates a schematic of another illustrative embodiment of a disposable article for filtration of menstrual fluid in situ. As shown, article 200 can be a tampon with an overall shape and size of a conventional tampon. Article 200 may include prefilter 202, positioning element 204, sample collection matrix 206, barrier 218, receptacle 208, impermeable layer 210, impermeable layer 212, first removal pull 216, and second removal pull 214. Article 200 may have an absorbency rating of less than 6 grams, 6 to 9 grams, 9-12 grams, 12-15 grams, or 15-18 grams. Article 200 may have compressed and non-compressed dimensions matching those of one or more commercially available tampons. For example, article 200 may be 5.5 cm in length and 1.0 cm in diameter in its compressed form, and may expand laterally by an additional 1.5 cm upon wetting. In other examples, article 200 may be 2-7 cm in length and 0.5-1.5 cm in diameter in the compressed form, and may expand 0.5-5 cm laterally/axially upon wetting.

Prefilter 202 may be constructed of a relatively loose cotton/polymer fiber web or weave configured to allow passage of liquids while retaining tissue and mucus. For example, prefilter 202 may have an average pore size within the range of 20-200 µm, 10-100 µm, or 50-500 µm. Prefilter 202 may be positioned at the top of article 200, such that it would be positioned near the cervix during use to absorb menstrual fluid.

After insertion of article 200 into the vagina, menstrual fluid may flow downwardly from the cervix into prefilter 202. As prefilter 202 becomes saturated, the fluid component of the menstrual fluid and smaller particles (e.g., erythrocytes) may then flow from prefilter 202 into sample collection matrix 206 and positioning element 204 by gravitational force and/or capillary action.

Positioning element 204 may be an absorbent material (e.g., cotton/nylon) and designed to expand axially or laterally in response to absorption of fluids, as in conventional tampons. Expansion of positioning element 204 may aid retention of the article within the vagina.

Sample collection matrix 206 may be a porous matrix constructed of cotton fibers with an average pore size of 0.01-5 µm. Barrier 218 may be a layer of non-porous or hydrophobic material (e.g., plastic or polymer, hydrophobic gel, or silicone) positioned along the vertical sides of sample collection matrix 206 at the interface between sample collection matrix 206 and positioning element 204. For example, barrier 218 may be a hollow plastic cylinder with a height of 2.5 cm, a diameter of 1 cm, and a thickness of 1.5 mm. Sample collection matrix 206 and receptacle 208 may be inserted into the hollow plastic cylinder, which may then be wrapped or compressed with positioning element 204 and prefilter 202 to form the tampon. The prevention of fluid exchange between positioning element 204 and sample collection matrix 206 allows menstrual fluid to flow into both components. This may help to maintain the position of article 200 within the vagina while allowing some of the menstrual fluid to enter sample collection matrix 206.

Menstrual fluid entering the upper surface of sample collection matrix 206 may flow by capillary action into receptacle 208, which is placed inside of sample collection matrix 206. Receptacle 208 may be constructed of cotton and/or polymer fibers. Receptacle 208 may include a barrier at the bottom, such as an impermeable layer 210, to prevent leakage. Likewise, sample collection matrix 206 may include a barrier at the bottom, such as an impermeable layer 212, to prevent leakage. Impermeable layers 210 and 212 can be constructed of silicone, a non-porous thermoplastic material, or other deformable and biocompatible material. Impermeable layers 210 and 212 may produced by dipping, spraying, soaking, or otherwise applying a hydrophobic substance, such as a silica gel, to the lower ends of receptacle 208 and sample collection matrix 206. Alternatively, the hydrophobic barrier and impermeable layers 210/212 can be provided by inserting the receptacle 208 and sample collection matrix 206 into a thin sleeve of plastic sealed at the bottom and coupled at the top to prefilter 202.

First removal pull 216 and second removal pull 214 can be cords constructed of cotton, nylon, or other materials as in conventional tampon cords. When the tampon has been used and is ready to be discarded, first removal pull 216 may provide for convenient removal of receptacle 208. The filtered fluid within receptacle 208 may then be used in one or more biological assays (e.g., by placing the upper end of receptacle 208 into contact with a detection matrix). Applying downward pressure on first removal pull 216 may pull receptacle 208 from article 200, leaving article 200 in place. Sample collection matrix 206 may also be partially or entirely removed with receptacle 208. Alternatively, sample collection matrix 206 may remain in place within article 200 as receptacle 208 is removed.

Second removal pull 214, which is coupled at opposite ends to receptacle 208 and to prefilter 202, may be brought into reach as receptacle 208 is removed. Second removal pull 214 may be pulled or cut from receptacle 208. Second removal pull 214 may then be pulled downward to remove the remaining components of article 200 in the same manner as for a conventional tampon. After removal, receptacle 208 may be placed into capillary contact with a detection matrix or other analyte sensor component for analysis of the fluid sample.

In other examples, receptacle 208 may be a detection matrix. In one such example, receptacle 208 may be a rolled sheet of membrane (e.g., a rolled nitrocellulose membrane) positioned within an interior void of sample collection matrix 206. A first detection reagent (e.g., an antibody to a target analyte, coupled to a colored polymer particle) may be provided in anhydrous form within sample collection matrix 206, between sample collection matrix 206 and the membrane, or between layers of the membrane (i.e. applied to the membrane prior to rolling). A second detection reagent (e.g., a second antibody to the target analyte) may be immobilized on an outer surface of the membrane. A capture reagent (e.g., an antibody to the first detection reagent) may also be immobilized on the outer surface of the membrane. The detection matrix, detection reagents, and capture reagent may operate as described with reference to lateral flow assays (see above). Therefore, after article 200 is used in the manner of a conventional tampon, receptacle 208 can be removed from article 200 as described above and unrolled to view the results of the assay.

Figure 3A:
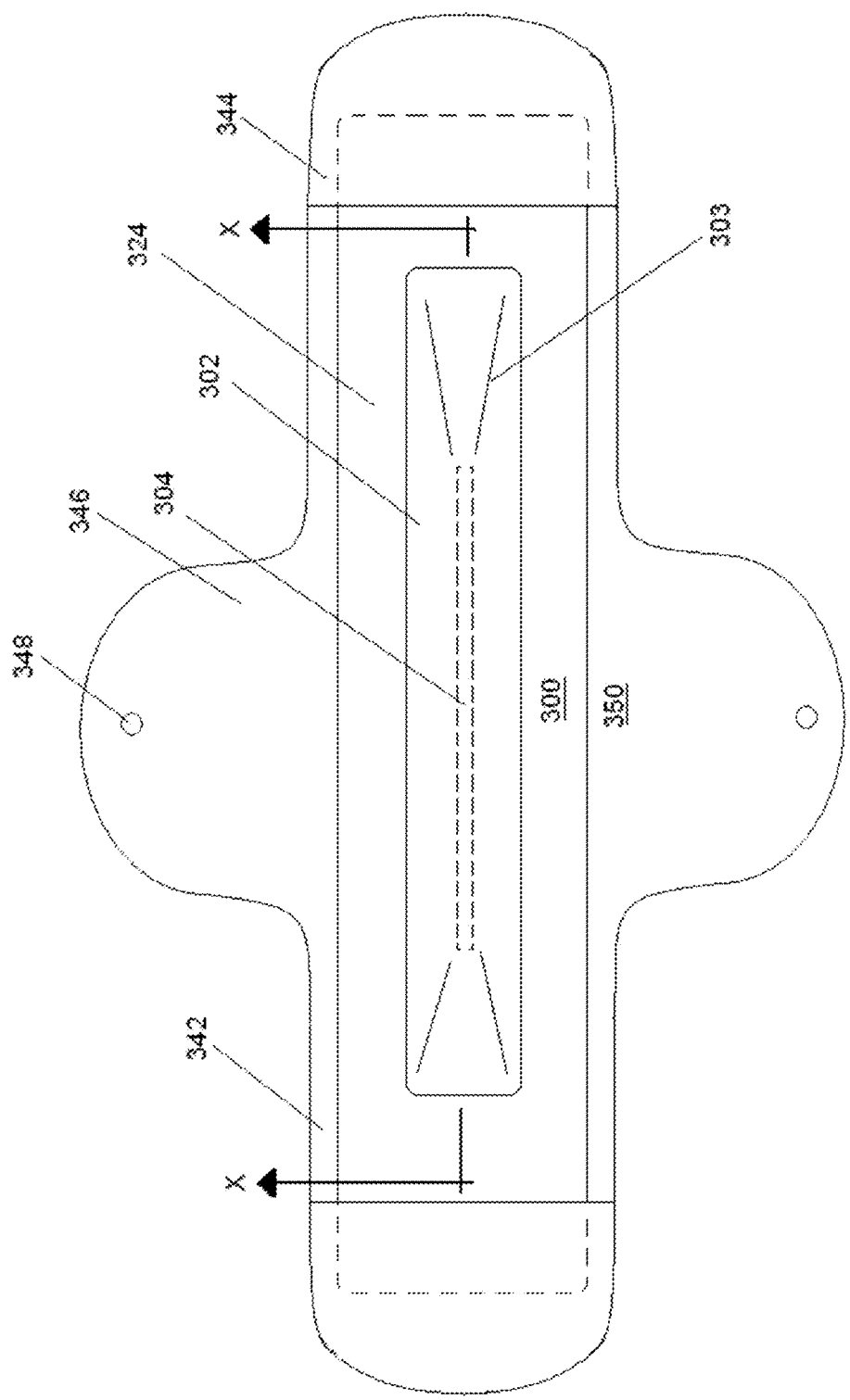
FIG. 3a illustrates a plan view of an illustrative embodiment of a disposable article for filtration of menstrual fluid in situ.
Figure 3B:
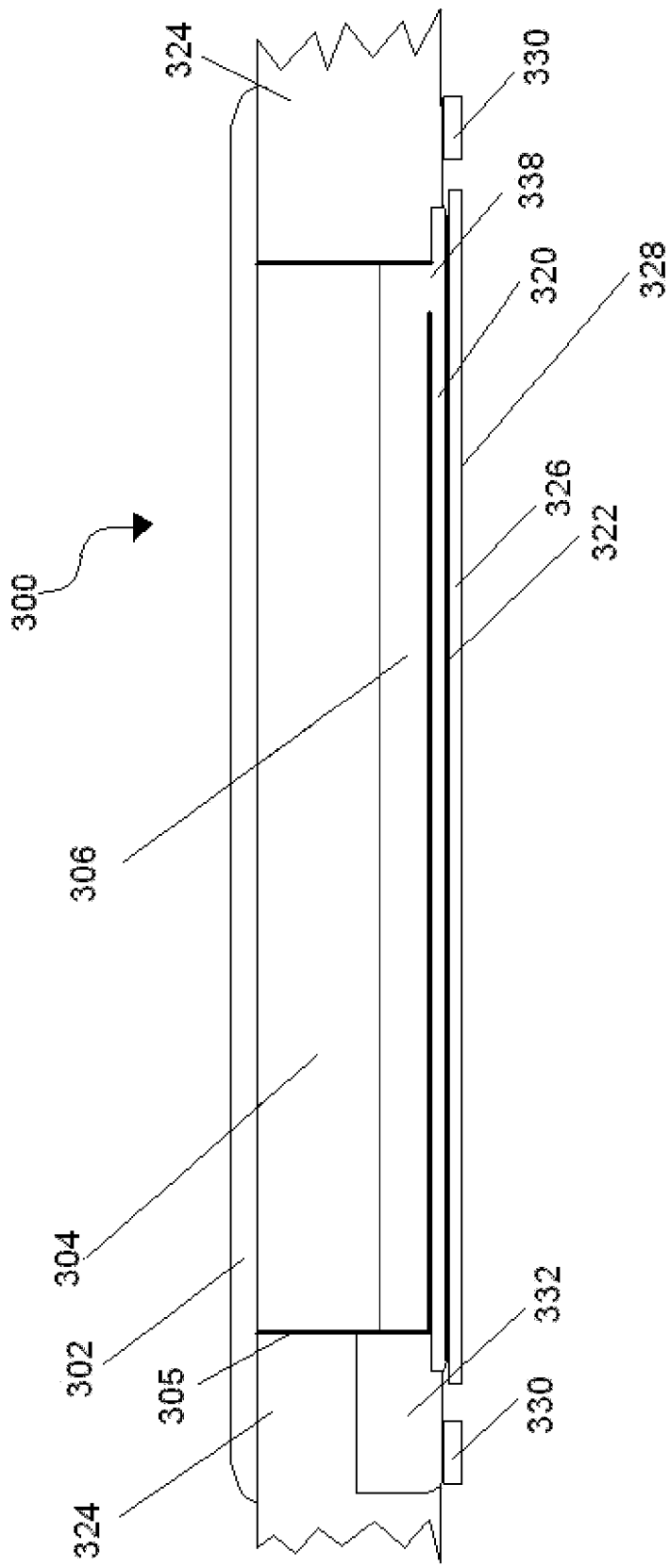
FIG. 3b illustrates a sectional view of the disposable article of FIG. 3a taken along lines X-X.

A prefilter, sample collection chamber, receptacle, and/or other components of an analyte sensor may also be integrated into a sanitary napkin. FIG. 3a illustrates a plan view of an illustrative embodiment of a holder for a disposable article with integrated analyte sensor components. FIG. 3b illustrates a sectional view of the disposable article of FIG. 3a taken along lines X-X.

Disposable article 300, provided in the form of a sanitary napkin, may be retained in a garment by holder 350. Disposable article 300 may include prefilter 302, sample collection matrix 304, and overflow pad 324. Additional description of disposable article 300 and components thereof is provided in FIG. 3b and the accompanying text below.

As illustrated in FIG. 3a, holder 350 may include base 342 with pockets 344 at both ends. Optionally, one or more extensions 346 may extend laterally from the sides of base 342 Extensions 346 may be configured to overlap or wrap around the crotch area of an undergarment. Base 342, pockets 344, and extensions 346 may be either moisture-resistant or absorbent, and may be constructed from one or more layers of a flexible fabric (e.g., woven cotton/polymer fibers), polymer, plastic, paper, or other materials known or used commercially for constructing feminine hygiene articles. Base 342 may be sized in accordance with standard sanitary napkin dimensions. For example, base 342 may be 10-30 cm in length and 5-20 cm in width.

In some examples, holder 350 may include one or more fasteners 348 (e.g., snaps, tape, and/or hook and loop fasteners) positioned along the bottom, around the edges, or along the sides of holder 350. As shown, fasteners 348 may be placed at the outer ends of extensions 346. Fasteners 348 may include but are not limited to one or more snaps, ties, tapes, hook and loop fasteners, or adhesives. Fasteners may be provided on the bottom surface or edges of the sanitary napkin and/or holder, and may be used to fasten the holder to an undergarment and may hold the sanitary napkin in position during wear. Examples of fasteners, holders, fastener arrangements, and methods of fastening sanitary napkins to undergarments include those known in the art and used by manufacturers of sanitary napkins.

Disposable article 300 may be placed into holder 350 with the longitudinal ends of disposable article 300 inserted into pockets 344. In the illustrated example, disposable article may be 20 cm in length and 6 cm in width, with a thickness of 1.5 cm. Pockets 344 may retain the article in position to receive a flow of menstrual fluid. In some examples, holder 350 is not provided, and disposable article 300 is instead retained by another mechanism, such as by an adhesive on the bottom of sanitary napkin 300 (see e.g., FIG. 3b).

FIG. 3b illustrates a cutaway view of disposable article 300 taken along the axis X-X of FIG. 3a. Disposable article 300 may include prefilter 302, sample collection matrix 304, and overflow pad 324 (see also FIG. 3a). In addition, disposable article 300 may include receptacle 306.

Overflow pad 324 may be provided in the general shape and dimensions of a conventional sanitary napkin (e.g., 20-38 cm in length, 0.5-10 cm in width, 0.1 cm-4 cm thick). Overflow pad 324 may be constructed from cotton/polymer fibers or other absorbent materials known and used in the manufacture of sanitary napkins. Overflow pad 324 may include an interior void extending through the thickness of overflow pad 324 from the top surface to the bottom surface. For example, overflow pad 324 may include an interior void measuring 8 cm in length, 1 cm in width, and extending through the full thickness of overflow pad 324 (e.g., 4 mm). Sample collection matrix 304 may be a porous matrix measuring 8 cm in length, 1 cm in width, and 0.1-1 mm thick, and may be positioned within the void. Overflow pad 324 may be coupled to one or more positioning elements 330, which may be used for coupling article 300 to an undergarment. In some examples, positioning elements 330 may be adhesive tape.

Prefilter 302 may be positioned over the surface of sample collection matrix 304 and may extend onto the upper surface of overflow pad 324. Prefilter 302 may be embossed, crushed, heated, or printed to form surface channels 303 (see FIG. 3a). Surface channels 303 may be arranged to direct a flow of menstrual fluid toward sample collection matrix 304. Examples of such depressions/channels are described in U.S. Pat. No. 4,795,455 to Luceri and Lukjanczuk, which is incorporated by reference herein.

Prefilter 302 may be a layer of polymeric web with conical pores of various dimensions as previously described. In one example, prefilter 302 may have a pore diameter on the top (upstream) surface within the range of 20-200M and a pore diameter on the bottom (downstream) surface within the range of 200-500 μm. Therefore, prefilter 302 may be permeable to liquids, erythrocytes, and bacterial/yeast/protozoan cells, but may trap or exclude larger solids such as mammalian tissue. Prefilter 302 may also exclude or retain viscous fluids (e.g., mucus), thereby preventing clogging of the underlying components.

Prefilter 302 may be coupled to sample collection matrix 304 and/or overflow pad 324 by any of the methods described above. Prefilter 302 may be provided as a top layer positioned over sample collection matrix 304. In the illustrated example, prefilter 302 is shown extending over the upper surface of sample collection matrix 304 and over a portion of the upper surface of overflow pad 324. In other examples, prefilter 302 may cover most or all of upper surface of overflow pad 324. In still other examples, prefilter 302 may extend only across the upper surface of sample collection matrix 304 (see e.g., FIG. 1). Prefilter 302 may also be pre-treated with a wetting agent as previously described.

Sample collection matrix 304 may include an absorbent and/or porous material, as discussed above with reference to sample collection matrices. Sample collection matrix 304 may be disposed between prefilter 302 and receptacle 306 in a stack. In some examples, sample collection matrix 304 may be an asymmetric membrane with pore diameters in the range of 5-20 μm at the upper (upstream) surface and pore diameters in the range of 0.05-5 μm at the lower (downstream) surface. In other examples, sample collection matrix 304 may be a stack of porous membranes, a glass fiber pad, or a cotton or cloth pad.

Receptacle 306 may be coupled to sample collection chamber 306 as described above. Receptacle 306 may be a layer of cellulose, such as a cellulose membrane or stack of cellulose membranes. In some examples, receptacle 306 may be provided in the same or similar dimensions as sample collection matrix 304. Alternatively, receptacle 316 may be constructed of another permeable medium such as a polyurethane foam. Receptacle 306 may be positioned below and in contact with sample collection matrix 304 to form a stack. In some examples, receptacle 306 may be provided in the same or similar dimensions as sample collection matrix 304. A non-porous or hydrophobic barrier 305 may be adhered to the sides and bottom of the stack. For example, barrier 305 can be a plastic film or polymer sheet. Barrier 305 may be continuously sealed to an outer surface (e.g., along the outer edges) of the sample collection matrix to form a pocket. The receptacle may be disposed within the pocket between sample collection matrix 304 and barrier 305.

As illustrated, aperture 338 may be formed in barrier 305 by cutting or ablating a portion of barrier 305 with a machine or laser. Aperture 338 may allow fluids to flow from receptacle 304 to detection matrix 320 by capillary action, gravitational force, and/or applied pressure (e.g., as the user sits or walks while the article is in use).

Optionally, solvent chamber 332 may be provided adjacent to receptacle 302 at the opposite end of aperture 338. Solvent chamber 332 may be a blister pack or other hollow receptacle containing a solvent for diluting or reconstituting the fluid component in receptacle 306, generating a reaction product, and/or saturating receptacle 306 to aid capillary flow into detection matrix 320. In some examples, solvent may be released from solvent chamber 332 into receptacle 306 by squeezing, twisting, or puncturing solvent chamber 332. In other examples, a portion of solvent chamber 332 may be coupled to absorbent pad 324 such that removal of absorbent pad 324 causes leakage or rupture of solvent chamber 332.

Receptacle 306 may be coated or otherwise provided with a first detection reagent in an anhydrous form. In some examples, the first detection reagent may include an enzyme or enzyme substrate. Alternatively, the first detection reagent may be an antibody-indicator conjugate such as a mouse antibody coupled to a dyed latex particle.

Detection matrix 320 may be a cellulosic or polymer membrane provided with an immobilized detection reagent, a capture reagent, and/or an indicator such as a dye in an anhydrous form. Detection matrix 320 may have the same or similar dimensions as receptacle 306. Alternatively, detection matrix 320 may be provided in other dimensions. In the illustrated example, detection matrix 320 is a nitrocellulose membrane 8.5 cm in length and 10 mm in width. In some examples, receptacle 306 and detection matrix 320 may be a continuous strip of porous medium (e.g., cellulose membrane). In other examples, receptacle 306 and detection matrix 320 may be separate components.

Detection matrix 320 may be in fluid communication with sample collection matrix 304 at a first end (e.g., near aperture 338). Detection matrix 320 may also be in contact with a porous or absorbent component such as overflow pad 324 (e.g., at the opposite end).

Disposable article 300 may be used in the manner of a conventional sanitary napkin. Menstrual fluid may flow downward through prefilter 302 and into sample collection matrix 304 by capillary action and gravitational force. Cells and other particles may be retained within or above sample collection matrix 304. The liquid component of the menstrual fluid may flow downward into receptacle 306 by capillary action and gravitational force. The liquid component may mix with the first detection reagent as it is drawn through the receptacle, allowing the first detection reagent to bind target analytes in the liquid. As receptacle 306 becomes saturated, the mixed liquid may be drawn into detection matrix 320 by capillary action.

In other examples, receptacle 306 may be physically separated from detection matrix 320 until another component is moved. This may be useful for assays that are time-sensitive or rapid. In addition, the first detection reagent may be adsorbed onto a first portion of detection matrix 320. In one such example, overflow pad 324 may be adhered to one end of an adhesive tape, with the other end of the adhesive tape adhered to the outer surface of barrier 305 and covering aperture 338. When the sanitary napkin is to be changed/discarded, overflow pad 324 may be pulled upward and away from the disposable article 300. This may cause the adhesive tape and some or all of the layers overlying receptacle 306, such as prefilter 302 and overflow pad 324, to be removed from receptacle 306 and/or sample collection matrix 304 as a single unit. Sample collection matrix 304 may remain in position over receptacle 306 as other components are removed, preventing contamination of the liquid within the receptacle. Barrier 305 may prevent leakage of fluid from the remaining components after removal of overflow pad 324.

Disposable article 300 may include an indicator disposed or immobilized on the bottom surface of detection matrix 320. As the mixed fluid component flows by capillary action through detection matrix 320, a reaction product (e.g., hydrogen peroxide) may interact with the indicator to produce a visible indication of target analyte presence (see e.g., FIG. 6a-6c). For example, a reaction product may react with an indicator to form a colored, insoluble chemical species that is deposited/visible on the bottom surface of detection matrix 320 in proportion to the concentration of the measured/target analyte.

In one example, an analyte sensor to measure cholesterol essentially as described by Allen (1990) may be provided in a feminine hygiene product to monitor cholesterol via menstrual fluid. In this example, receptacle 306 may be provided with a first detection reagent such as horseradish peroxidase (HRP) in anhydrous form. A second detection reagent, which includes cholesterol esterase and cholesterol oxidase, is immobilized on a first portion of the bottom surface of detection matrix 320 at the end of the membrane nearest to aperture 338. A peroxidase substrate such as 3-methyl-2-benzothiazolinone hydrazone with N,N-dimethylaniline (MBTH-DMA) is immobilized on some or all of the remaining bottom surface of detection matrix 320.

The fluid component of the menstrual fluid mixes with the HRP in receptacle 306 and flows into detection matrix 320 through aperture 338. As the mixed fluid flows through the first portion of detection matrix 320, cholesterol in the fluid component is converted to hydrogen peroxide by the cholesterol esterase and cholesterol oxidase. As the fluid is drawn through the portion of the membrane with the immobilized MBTH-DMA, the hydrogen peroxide reacts with the MBTH-DMA in the presence of the HRP. The reaction produces a colored band on detection matrix 320. The length of the colored band is proportional to the amount of hydrogen peroxide, and can therefore be correlated to the concentration of cholesterol in the fluid component tested.

In this example, the detection may be a time-sensitive process requiring the user to read the result within a certain length of time after the fluid component reaches detection matrix 320. Therefore, analyte sensor may be provided with a removable barrier between reservoir 306 and detection matrix 320 as described above. This may allow the user to remove the barrier and begin the assay when the user is ready to discard the sanitary napkin.

Display 326 may be provided along the bottom of detection matrix 320. Display 326 can be a strip of paper, plastic, and/or any flexible material. Display 326 may be coupled to detection matrix 320 by a coupling element 322 disposed between detection matrix 320 and display 326. Coupling element 322 may be an adhesive tape positioned between the outer edges of display 326 and a bottom surface of overflow pad 324 and/or detection matrix 320.

In some examples, as a visible reaction product is formed on the bottom of detection matrix 320, it may be deposited on display 326. Alternatively, one or more indicators may be coupled to display 326 and may produce a visible indication of target analyte presence/concentration. Display 326 may then be removed from the analyte sensor after the assay is completed, allowing the user to discard the remainder of disposable article 300. Display 326 may include a preservative to retain the visible indication for a period of days, weeks, months, or even years.

In other examples, display 326 may be a sheet of opaque or semi-translucent material, such as paper or plastic. As further illustrated in FIGS. 6a-6c, one or more portions of display 326 may be removed and/or replaced with a clear material (e.g., cellophane) to provide a view of detection matrix 320, and thus the results of an assay. In the illustrated example, display 326 may be 4 cm in width, 9 cm in length, and 1 mm thick. Display 326 may also include an interior cut-out portion forming a window over the detection matrix (see e.g., FIGS. 6a-6c). Display 326 may have outer surface 328 with a printed calibration scale or other information, as further described in FIGS. 6a-6c and the accompanying text.

Figure 4A:
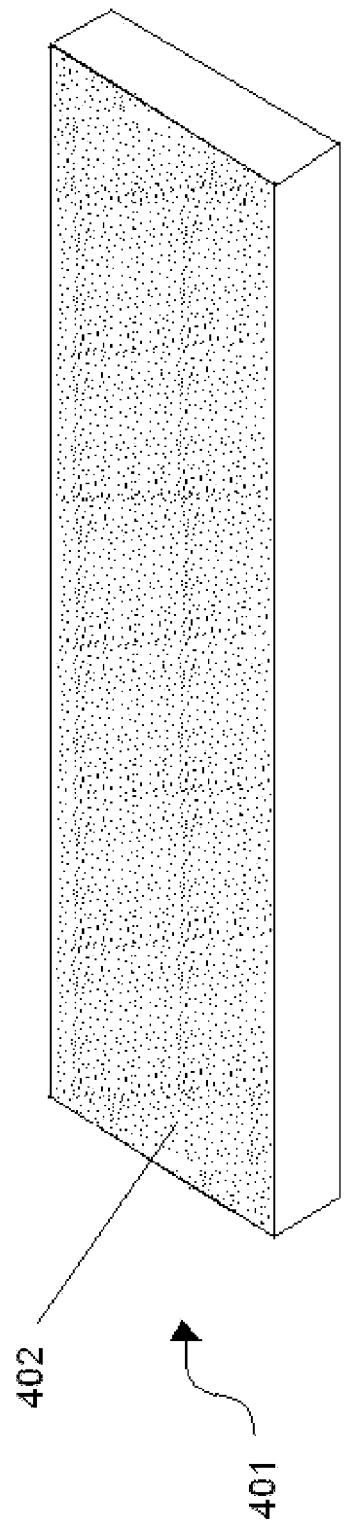
Figure 4B:
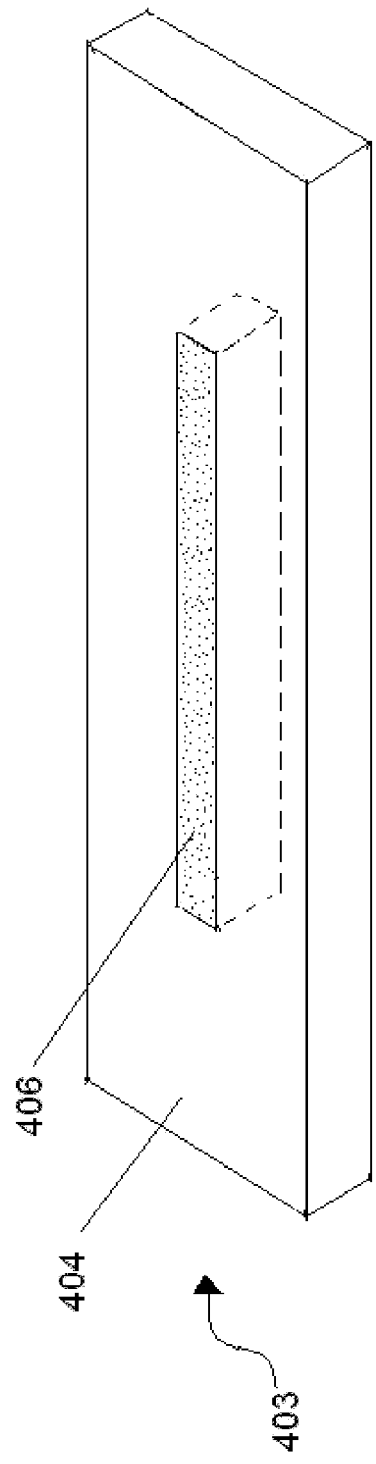

FIGS. 4a-4c illustrate perspective views of illustrative embodiments of sample collection matrices for filtration of menstrual fluid in situ. A sample collection matrix (e.g., sample collection matrix 401, 403, and/or 405) may be a porous matrix with a plurality of pores sized to exclude erythrocytes and/or other mammalian cells. The pores may allow extracellular fluid to pass from the first surface (top) to the second surface (bottom). Some or all of the pores may have a diameter that is less than the diameter of a mammalian erythrocyte, such as a diameter of 0.001-0.01 µm, 0.01-0.1 µm, 0.1-1 µm, or 1-5 µm. As another example, some or all of the pores may be less than 1 micrometer (1 µM) in diameter. In some embodiments, a sample collection matrix may be an asymmetric membrane or asymmetric membrane stack with larger pores (e.g., 5-50 µm in diameter) at a first surface or first membrane and smaller pores (e.g., 0.001-0.01 µm, 0.01-0.1 µm, 0.1 to 1.0 µm, or 1.0 to 5.0 µm in diameter) at a second surface or underlying membrane to retain small particles such as cell fragments while preventing entry of larger particles into the sample collection matrix.

As shown, a sample collection matrix may be provided in various configurations. A sample collection matrix may be a block of porous material, such as filter 401 (FIG. 4a). For example, filter 401 may have a base 402 made of glass microfiber, 0.5 cm thick and with a length and width of 0.5-3.0 cm. Alternatively, a sample collection matrix may have a single block or stack of porous material 406 with a length and width of 2.0 cm and a height of 2 mm, embedded or contained within a base 404 of similar dimensions (sample collection matrix 403, FIG. 4b). For example, base 404 may be a hollow flexible plastic chamber with a length and width of 2.0 cm and a height of 2 mm, at least partially enclosing a stack of porous membranes with similar dimensions. In another example, a sample collection matrix may have a base 408 and two or more separate sample collection matrix sections 410 and 412 (sample collection matrix 405, FIG. 4c). A sample collection matrix with two or more porous structures may be included in a menstrual pad as a component of an integrated analyte sensor in order to detect two or more analytes that display cross-reactivity. Two or more receptacles and/or detection matrices may likewise be provided for separate analysis of the liquid samples. Alternatively, such a sample collection matrix may be included in a menstrual pad as a component of an integrated analyte sensor in order to provide a control sample to assess the reliability of the assay results.

Figure 5A:
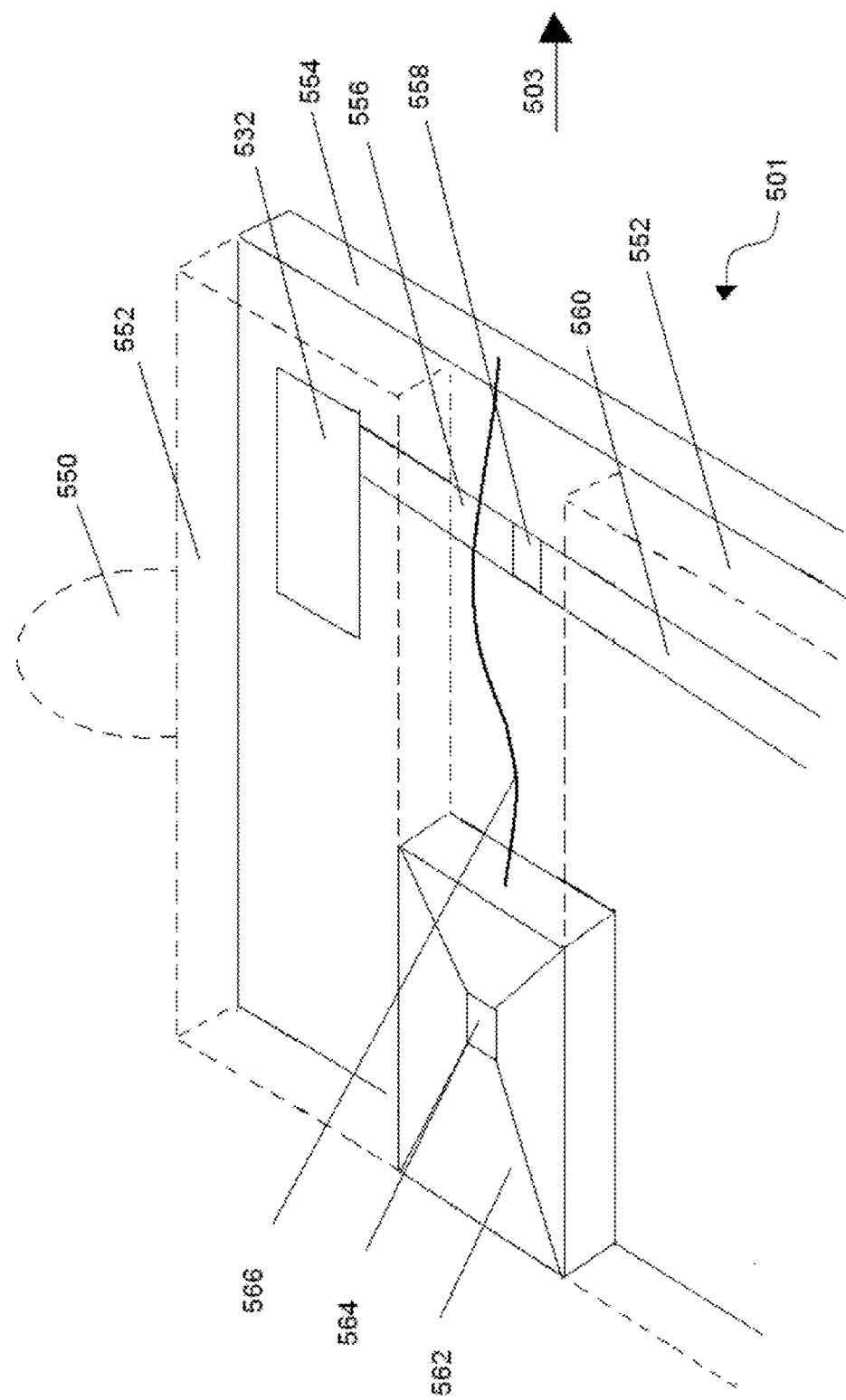
FIGS. 5a-5b illustrate partial cutaway views of disposable articles with a movable sample chamber.
Figure 5B:
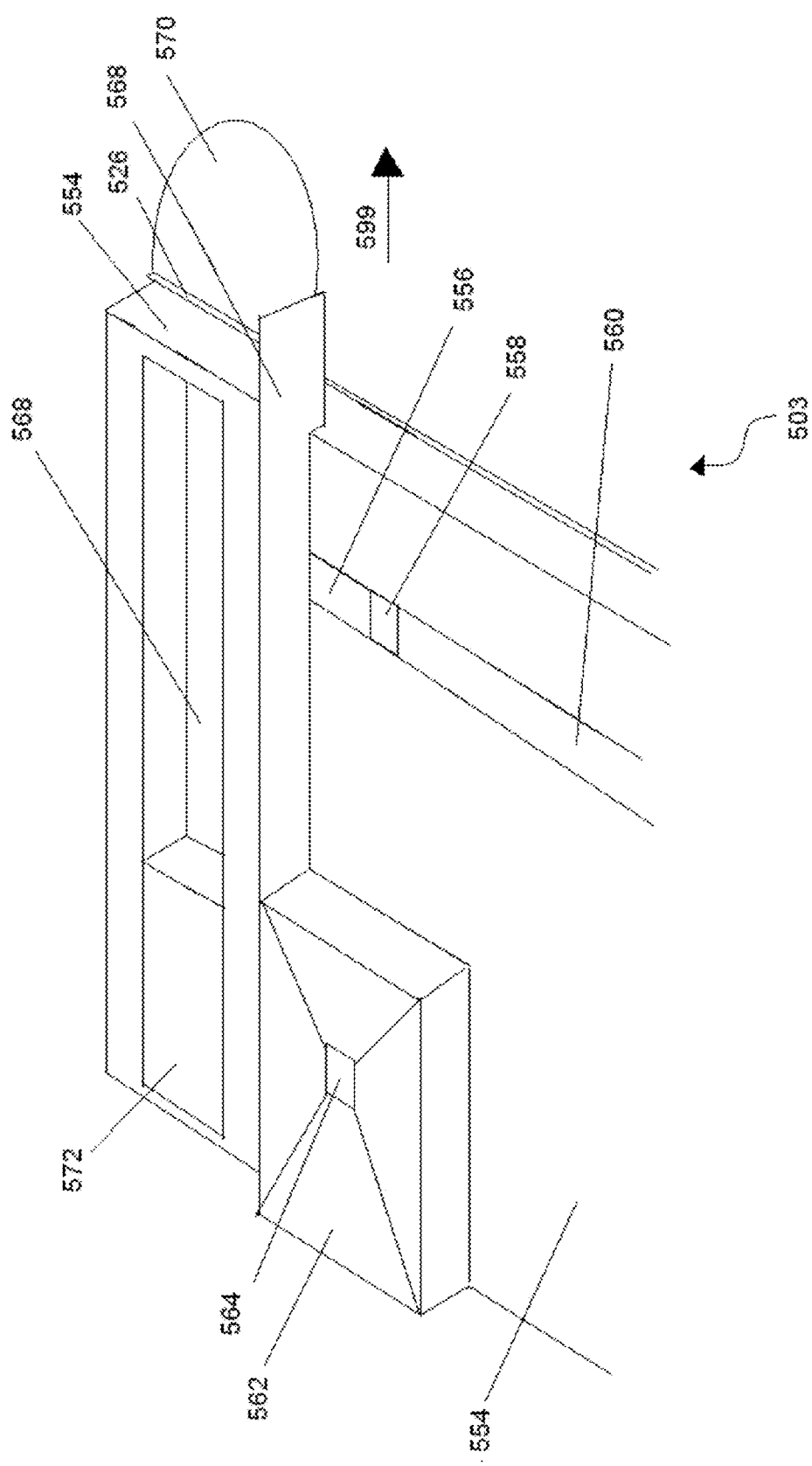

FIGS. 5a-5b illustrate partial cutaway views of illustrative embodiments of disposable articles with a movable sample chamber. A movable sample chamber may be shifted from a 'collection' area to a 'test' area in order to isolate the test area from the menstrual fluid until testing is ready to be performed. A 'collection area' is the area in which a sample collection chamber/matrix is retained during use of the article to receive a flow of menstrual fluid. A 'test' area is an area in which downstream analyte sensor components, such as a detection matrix, are located. For example, a collection area and a test area may be located on opposite sides of a menstrual pad as shown in FIGS. 5a and 5b. Providing separate collection and test areas with a movable sample collection chamber/matrix may be appropriate for a timed assay, an assay that requires user interaction, and/or an assay with a display of results that remains accurate/readable for a short period of time.

FIG. 5a illustrates a disposable menstrual pad 501 with an integrated analyte sensor. In FIG. 5a, menstrual pad 501 is shown with sample chamber 562 movably coupled to analyte sensor 554. The position of surrounding layer 552 is shown in dashed lines. Surrounding layer 552 may be an absorbent layer and/or may be sealed along a bottom surface to prevent absorbed menstrual fluids from contacting analyte sensor 554. Surrounding layer 552 may include tab 550. Tab 550 may be coupled along a bottom surface of surrounding layer 552 and/or one or more other layers. For example, tab 550 may be pulled after analyte detection is complete in order to remove surrounding layer 552 and/or sample chamber 562 from analyte sensor 554.

Sample chamber 562 may include filter 564 and filter repositioning element 566, such as a string, a tab, etc. Sample chamber 562 may be shaped or provided with channels as described above to direct menstrual fluid toward sample collection matrix 564. For example, sample collection matrix 564 may be a porous matrix disposed toward the center of sample chamber 562, and sample chamber 562 may have one or more raised peripheral edges to create a funnel or other similar effect. In this example, sample collection matrix 564 may be a stack of membranes, the top membrane with pore diameters within the range of 5-50 µm and the bottom membrane having pore diameters within the range of 0.2-5 µm. In other examples, sample collection matrix may include a cotton fiber pad or other relatively porous material over an asymmetric membrane. Sample collection matrix 564 may also perform the function of a receptacle, and may retain a volume of the filtered liquid component of menstrual fluid while in the collection area.

Also shown are solvent chamber 532 coupled to first detection pad region 556, detection pad sample area 558, and second detection pad region 560. In operation, a user may move sample chamber 562 in the direction of arrow 503 to begin the assay. A liquid component of menstrual fluid may flow through the bottom of filter 564 onto detection pad sample area 558. The user may squeeze, break, or otherwise disrupt solvent chamber 532, resulting in a flow of solvent across first detection pad region 556. One or both of these components may include a reaction medium, a detection reagent, an indicator, an enzyme, a preservative/stabilizer, etc. The solvent may redissolve a dried liquid component sample and/or instigate a reaction. A visible indication of analyte detection may be shown on second detection pad region 560. The visible indication may be viewed through a window region along the back of analyte sensor 554 (see e.g., FIGS. 6a-6c).

FIG. 5b shows another example of sample chamber 562 movably coupled to an analyte sensor 554. Pull tab 568 may be coupled to sample chamber 562, and may also provide a barrier between movable solvent chamber 572 and first detection pad region 556. Pulling pull tab 568 may move both solvent chamber 572 and sample chamber 562 in the direction of arrow 599.

Pulling pull tab 568 may also remove an adhesive tape or other barrier from the bottom of solvent chamber 572 and/or sample chamber 562. In one example, a length of adhesive tape may be provided in a length that is slightly less than that distance between the sample area and testing area. The tape may be folded in half to bring the opposite ends together with the non-adhesive surface in the center and the adhesive surface exposed. One end of the folded tape may be placed over an aperture or gap in the bottom of the solvent/sample chamber, with the adhesive coupling the tape to the chamber(s). The other end of the folded tape may be pressed onto the surface of the underlying analyte sensor 554 below the solvent/sample chamber. When pull tab 568 is pulled, the tape may be pulled taut and may then be released from the bottom of the solvent/sample chamber as the solvent/sample chamber reaches the test area. This may release fluids from the chamber(s) to begin the detection of the target analyte.

The detection of the target analyte may proceed as described above. Once the detection has been completed, the results may be viewed through or on display 526 as further described above. Display 526 may include tab 570, which may be accessible to a user at one end or side of the disposable menstrual pad. In some examples, display 526 may be removed from the remaining components of the analyte sensor by pulling tab 570. Display 526 may have a configuration similar to that of display 326, shown in FIG. 3b.

As further illustrated in FIGS. 6a-6c, a printed window or other viewing area may be provided on the underside of a menstrual pad. In some embodiments, a menstrual fluid analyte sensor may provide a displayed result without separate accessories, such as a separate calibration scale. For example, a calibration curve or other assay information (e.g. numbers, a scale, instructions, interpretation guidelines, etc.) may be printed onto the pad as part of the manufacturing process with an ink-jet printing device.

FIGS. 6a-6c illustrates plan views of an illustrative embodiment of a menstrual fluid assay display. FIG. 6a shows a display with display surface 602, one or more printed surface portions 606, display portal 604, and visible indication of analyte detection 608. In some examples, visible indication of analyte detection 608 may be on a detection matrix and may be viewed through display portal 604. In other examples, visible indication of analyte detection 608 may be on the display itself.

Printed surface portion 606 may include a calibration scale, a conversion chart, labels corresponding to analytes, instructions, and/or other information for facilitating interpretation of assay results. In FIG. 6a, the assay result may be read by comparing interface 610 at the farthest end of visible indication 608 to printed surface portions 606. Display portal 604 may include a cutout and/or clear portion along an analyte sensor and/or other component.

As shown in FIG. 6b, a display may include second display portal 614, second printed surface portion 616, second visible indication of analyte detection 618, and/or second interface 620. In some embodiments, two or more analytes may be detected using one analyte sensor. For example, one analyte sensor may have a display with two display portals. The first display portal may provide a view of a cholesterol detection/quantification assay result, while the second display portal may correspond to a control assay. A control assay may include an assay for a common component of blood and/or extracellular fluid, such as albumin, in order to determine whether the first assay result is unreliable due to sample dilution (e.g., with mucus, etc.). In another example, a control assay may include an assay to determine whether the reagents used in the first assay are performing within expected parameters.

FIG. 6c shows an alternative format for a display. A display surface 622 may include one or more printed surface portions having control portion 626 and target analyte portion 628. Results may be visible through portal 624 and may be displayed as individual non-mobile indications 630. These may vary by color and/or color intensity to provide additional information as to the relative concentrations of the target analytes.

Figure 7:
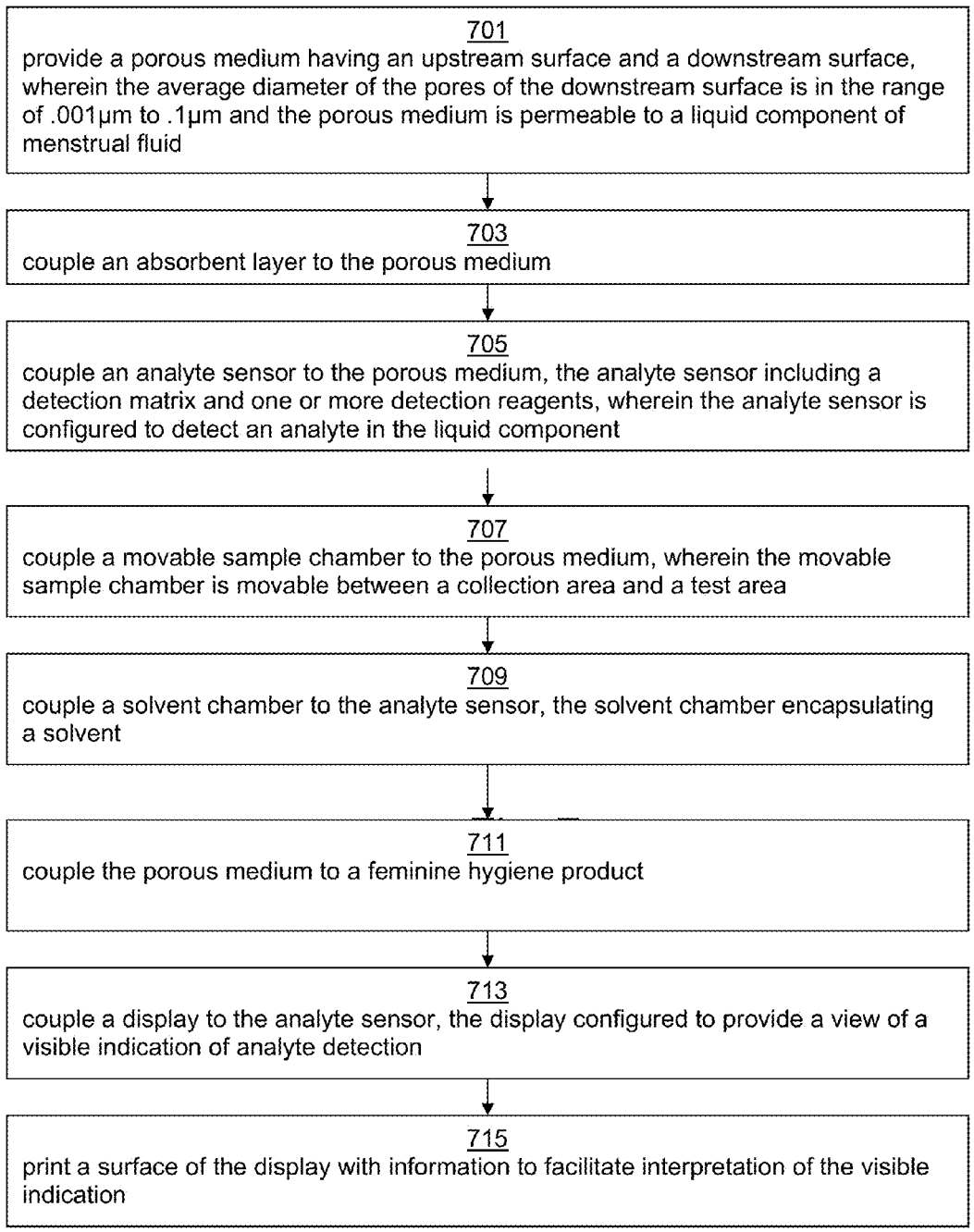
FIG. 7 illustrates a flow chart for manufacturing an in situ menstrual fluid assay system.

FIG. 7 illustrates a flow chart for an illustrative embodiment of a method of manufacturing an in situ menstrual fluid assay system. It will be appreciated that in some examples, various blocks may be eliminated, divided into additional blocks, and/or combined with other blocks. Processing for the illustrated method may start at block 701.

At block 701, a porous medium having an upstream surface and a downstream surface may be provided. The average diameter of the pores of the downstream surface may be in the range of 0.001 µm to 0.1 µm and the porous medium may be permeable to a liquid component of menstrual fluid. As discussed above, a porous filter may have a top/upstream surface with first plurality of pores of one diameter (e.g., 1-5 µM, 5-50 µm, or 50-500 µm) and a second plurality of pores of a second diameter (e.g., 0.001-0.1 µm, 0.1-1 µm, or 0.5-5 µm).

From block 701, the illustrated method may proceed to block 703. In block 703, an absorbent layer may be coupled to at least one surface of the porous medium. Coupling an absorbent layer to the porous medium (e.g., to the top, bottom, or one or more sides) may include placing the absorbent layer and porous medium into a sheath/sleeve, melting and/or heating the lateral edges of the porous medium and the absorbent layer, or using any one or more other chemical, mechanical, heat and/or solvent treatments known in the art for adhering woven/non-woven materials. Alternatively, the coupling may include placing the porous filter into the absorbent layer, into a cavity, depression, and/or other feature of the absorbent layer, and/or beneath the absorbent layer.

From block 703, the illustrated method may optionally proceed to block 705. In block 705, an analyte sensor may be coupled to the porous medium. The analyte sensor may include a detection matrix and one or more detection reagents, and the analyte sensor may be configured to detect an analyte in the liquid component. As described above, the analyte sensor may be coupled to the downstream surface of the porous medium, such as by placing the detection matrix into contact with the downstream surface of the porous medium or with a receptacle coupled to the porous medium. Alternatively, the analyte sensor may be coupled to the downstream surface of the porous medium, and retained in position by one or more components of a feminine hygiene product (e.g., an absorbent pad and/or movable sample chamber).

As discussed above, a receptacle may be coupled to a porous matrix and/or detection matrix. In some examples, a receptacle may be removably coupled to the analyte sensor. The detection matrix and/or receptacle may be provided with one or more detection reagents during or after manufacturing, such as by immersion/dip-coating, spraying, powder coating, or using other known methods for applying reagents to porous assay media. One or more detection/capture reagents may be immobilized on the detection matrix, provided in a solvent/solvent chamber, added in anhydrous form between two or more layers of a stack, and/or provided in or on a receptacle. The analyte sensor and porous matrix may be inserted within a cavity or void of a feminine hygiene product, such as a tampon, menstrual cup, or sanitary napkin, as discussed above.

From block 705, the illustrated method may optionally proceed to block 707. At block 707, a movable sample chamber may be coupled to the porous medium. The movable sample chamber may be movable between a collection area and a test area. In one example, a movable sample chamber may be provided in a sanitary napkin or tampon. In another example, a movable sample chamber may be provided with an integrated porous matrix. The sample chamber may be movable between a collection area positioned in the path of a flow of menstrual fluid and a test area positioned over a detection matrix or receptacle.

From block 707, the illustrated method may optionally proceed to block 709. At block 709, a solvent chamber may be coupled to the analyte sensor. The solvent chamber may encapsulate a solvent. As discussed above with reference to FIG. 3b, a solvent chamber may be placed within an absorbent layer and/or otherwise coupled to the analyte sensor. The solvent chamber may be movable. In some examples, repositioning or removal of the absorbent layer or other component may result in the release of solvent into the analyte sensor from the solvent chamber.

From block 709, the illustrated method may optionally proceed to block 711. At block 711, the porous medium may be coupled to a feminine hygiene product. The absorbent layer may be an absorbent pad of a feminine hygiene product such as a tampon or sanitary napkin, and coupling the porous medium to a feminine hygiene product may include placing the porous medium into a void or channel in the absorbent layer. The porous medium may be melted, heated, pressed, or treated with an adhesive for adhesion to the absorbent layer. Alternatively, the feminine hygiene product may lack an absorbent layer (e.g., a menstrual cup), and the porous medium may be coupled to the feminine hygiene product by placing the porous medium within a concavity or hollow of the product. In other examples, coupling the porous matrix and feminine hygiene product may include placing the porous medium beneath a prefilter (e.g., beneath a top sheet of a sanitary napkin). In still other examples, the porous matrix may be provided with a receptacle and adhesive tape, and coupling the porous matrix and feminine hygiene product may include pressing the adhesive tape onto the surface of a sanitary napkin.

From block 711, the illustrated method may optionally proceed to block 713. At block 713, a display may be coupled to the analyte sensor. The display may be configured to provide a view of a visible indication of analyte detection. Coupling the display to the analyte sensor may include reversibly coupling those components to allow the display to be removed after the assay. Alternatively, coupling the display to the analyte sensor may include providing a permanent coupling at one location, such as coupling the display to the detection matrix, and providing a reversible coupling at another location, such as between the detection matrix and the receptacle. In some embodiments, a detection matrix or display may include one or more electronic components and/or be endowed with operating logic configured to operate the analyte sensor, a microprocessor, a transceiver, and/or other components.

From block 713, the illustrated method may optionally proceed to block 715. At block 715, a surface of the display may be printed with information to facilitate interpretation of the visible indication. Printing may be performed by any device/method for producing a visual image using ink or alternatives, such as lithography, digital printing, ink-jet printing, or other devices/methods known in the art. Printing may be on any surface of the display. For example, printing may be on an inside surface of a clear or light-colored plastic display, and the printing may be read through the display without uncoupling the display from the analyte sensor. In another example, printing may be on the outer surface of a paper display, and may be arranged around a window through which the detection matrix may be viewed.

The herein-described subject matter sometimes illustrates different components or elements contained within, coupled to, or connected with, different other components or elements. It is to be understood that such depicted architectures are merely examples, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermedial components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or Figures, should be understood to contemplate the possibilities of including one of the terms, either of the terms, or both terms. For example, the phrase "A or B" will be understood to include the possibilities of "A" or "B" or "A and B."

Various operations may be described as multiple discrete operations in turn, in a manner that may be helpful in understanding embodiments; however, the order of description should not be construed to imply that these operations are order-dependent. Also, embodiments may have fewer operations than described. A description of multiple discrete operations should not be construed to imply that all operations are necessary. Also, embodiments may have fewer operations than described. A description of multiple discrete operations should not be construed to imply that all operations are necessary.

Although certain embodiments have been illustrated and described herein for purposes of description of the preferred embodiment, it will be appreciated by those of ordinary skill in the art that a wide variety of alternate and/or equivalent embodiments or implementations calculated to achieve the same purposes may be substituted for the embodiments shown and described without departing from the scope of the disclosure. Those with skill in the art will readily appreciate that embodiments of the disclosure may be implemented in a very wide variety of ways. This disclosure is intended to cover any adaptations or variations of the embodiments discussed herein. Therefore, it is manifestly intended that embodiments of the disclosure be limited only by the claims and the equivalents thereof.

What is claimed is:

1. A disposable menstrual fluid fractionation apparatus comprising:
    a porous matrix including an upstream surface with a first plurality of pores and a downstream surface with a second plurality of pores, the first and the second plurality of pores being permeable to a liquid component of a flow of menstrual fluid and the second plurality of pores being impermeable to a mammalian erythrocyte, and the average diameter of the second plurality of pores being less than the average diameter of the first plurality of pores, the first plurality of pores having an average diameter in the range of 5 µm to 50 µm and the second plurality of pores having an average diameter in the range of 0.001 µm to 5 µm;
    a receptacle coupled to the downstream surface of the porous matrix, the receptacle configured to receive a portion of the liquid component after passage of the flow of menstrual fluid through the porous matrix;
    a first detection reagent coupled to the porous matrix or the receptacle, the first detection reagent configured to interact with one or more second detection reagents of an analyte sensor to detect a target analyte in the liquid component; and
    a positioning element coupled to the porous matrix, the positioning element configured to retain the porous matrix in proximity to a flow of menstrual fluid, wherein the disposable menstrual fluid fractionation apparatus is configured to be coupled to a feminine hygiene product.

2. The disposable menstrual fluid fractionation apparatus of claim 1, wherein the first detection reagent comprises one or more of an antibody, an aptamer, or an enzyme.

3. The disposable menstrual fluid fractionation apparatus of claim 1, wherein the apparatus further comprises a detection matrix coupled to the receptacle, and wherein the detection matrix includes at least one of the one or more second detection reagents.

4. The disposable menstrual fluid fractionation apparatus of claim 1, wherein the apparatus further comprises an absorbent layer coupled to the porous matrix and a liquid-impermeable barrier disposed between the absorbent layer and the porous matrix, the absorbent layer configured to absorb a portion of the flow of menstrual fluid, and the liquid-impermeable barrier configured to prevent passage of the absorbed menstrual fluid from the absorbent layer to the detection matrix.

5. The disposable menstrual fluid fractionation apparatus of claim 1, further comprising a prefilter coupled to the upstream surface of the porous matrix, the prefilter having a third plurality of pores with an average diameter greater than the first plurality of pores, the prefilter being impermeable to mammalian tissue.

6. The disposable menstrual fluid fractionation apparatus claim 1, wherein the porous matrix includes one or more of an asymmetric microporous membrane or a stack of two or more porous membranes.

7. The disposable menstrual fluid fractionation apparatus of claim 1, wherein the average diameter of the second plurality of pores is in the range of 0.5 µm to 5 µm.

8. The disposable menstrual fluid fractionation apparatus of claim 1, wherein the positioning element includes one or more of an adhesive or an absorbent pad.

9. A non-invasive menstrual fluid analyte monitoring system comprising:
    an absorbent layer;
    a porous matrix coupled to the absorbent layer and including an upstream surface with a first plurality of pores and a downstream surface with a second plurality of pores, the first plurality of pores having an average diameter in the range of 5 µm to 50 µm and the second plurality of pores having an average diameter in the range of 0.001 µm to 5 µm, wherein the porous matrix is permeable to a liquid component of menstrual fluid and the second plurality of pores is impermeable to a mammalian erythrocytes;
    an analyte sensor operatively coupled to the porous matrix and including a detection matrix with an upstream end and a downstream end; and
    a first and a second detection reagent independently disposed between the upstream surface of the porous matrix and the downstream end of the detection matrix, the first detection reagent configured to interact with the second detection reagent to detect a target analyte in the liquid component of the menstrual fluid.

10. The system of claim 9, further comprising a solvent chamber coupled to the detection matrix, the solvent chamber encapsulating a solvent.

11. The system of claim 9, further comprising a liquid-impermeable barrier operatively coupled to the porous matrix and the analyte sensor, the liquid-impermeable barrier disposed between the porous matrix and the absorbent layer and configured to prevent fluid passage from the absorbent layer to the analyte sensor.

12. The system of claim 9, further comprising a positioning element coupled to the absorbent layer, the positioning element configured to retain the porous matrix in proximity to a flow of menstrual fluid.

13. The system of claim 9, wherein the analyte sensor further includes a display with a first surface and an opposite second surface, the first surface having a printed portion and the second surface being coupled to the detection matrix.

14. The system of claim 13, wherein the display is removable from the analyte sensor.

15. The system of claim 9, further comprising a holder configured to retain the absorbent layer and porous matrix against a garment.

16. The system of claim 9, wherein the porous matrix is at least partially surrounded by the absorbent layer.

17. The system of claim 9, further including a receptacle disposed between the porous matrix and the detection matrix, the receptacle being liquid permeable.

18. The system of claim 17, wherein the second detection reagent is coupled to the detection matrix and the first detection reagent is coupled to the porous matrix or the receptacle.

19. The system of claim 9, wherein the first detection reagent includes an indicator selected from the group consisting of a colored particle, a colloidal particle, an enzyme, and an enzyme substrate.

20. The system of claim 9, further comprising a prefilter coupled to the porous matrix and the absorbent layer, wherein the system is integrated within a feminine hygiene product.

21. The system of claim 13, wherein the printed surface portion comprises a calibration scale.

22. The system of claim 17, wherein at least one of the porous matrix or the receptacle is movably coupled to the analyte sensor and selectively positionable between a first position and a second position, the first position providing fluid communication with the detection matrix and the second position preventing fluid communication with the detection matrix.

23. A method for manufacturing a menstrual fluid assay, the method comprising:
    providing a porous medium having an upstream surface and a downstream surface, wherein the average diameter of the pores of the upstream surface is in the range of 5 µm to 50 µm, and wherein the average diameter of the pores of the downstream surface is in the range of 0.001 µm to 5 µm, the porous medium being permeable to a liquid component of menstrual fluid and selectively impermeable to one or more particles in the menstrual fluid;
    coupling a first detection reagent to the porous medium; and
    coupling an analyte sensor to the porous medium, the analyte sensor including a detection matrix and one or more second detection reagents, wherein the analyte sensor is configured to detect an analyte in the liquid component, and
    wherein the menstrual fluid assay is configured to provide a path of liquid flow from the downstream surface of the porous medium through the detection matrix.

24. The method of claim 23, further comprising coupling a display to the detection matrix, the display configured to provide a view of a visible indication of analyte detection by the analyte sensor.

25. The method of claim 23, further comprising coupling a solvent chamber to the analyte sensor, the solvent chamber encapsulating a solvent.

26. The method of claim 23, further comprising coupling the porous medium to a feminine hygiene product.

27. The method of claim 24, further comprising printing a surface of the display with information to facilitate interpretation of the visible indication.

* * * * *

UNITED STATES PATENT AND TRADEMARK OFFICE
CERTIFICATE OF CORRECTION

PATENT NO. : 8,911,988 B2
APPLICATION NO. : 13/202559
DATED : December 16, 2014
INVENTOR(S) : Miller Page 1 of 1

It is certified that error appears in the above-identified patent and that said Letters Patent is hereby corrected as shown below:

In the Specification

In Column 1, Line 5, delete "USC 371" and insert -- USC § 371 --, therefor.

In Column 4, Line 67, delete "one or" and insert -- one or more --, therefor.

In Column 10, Line 53, delete "chloride," and insert -- chloride), --, therefor.

In Column 10, Line 55, delete "Noniodet" and insert -- Nonidet --, therefor.

In Column 11, Line 29, delete "FIG. 3a-3b," and insert -- FIGS. 3a-3b, --, therefor.

In Column 21, Lines 1-2, delete "receptacle 304" and insert -- receptacle 306 --, therefor.

In Column 21, Line 6, delete "receptacle 302" and insert -- receptacle 306 --, therefor.

In Column 22, Lines 10-11, delete "FIG. 6a-6c)." and insert -- FIGS. 6a-6c). --, therefor.

In the Claims

In Column 30, Line 25, in Claim 6, delete "apparatus" and insert -- apparatus of --, therefor.

Signed and Sealed this
Sixteenth Day of June, 2015

Michelle K. Lee
*Director of the United States Patent and Trademark Office*